US011578100B2

(12) United States Patent
Cudic et al.

(10) Patent No.: US 11,578,100 B2
(45) Date of Patent: Feb. 14, 2023

(54) CYCLIC PEPTIDES, CYCLIC PEPTIDE CONJUGATES AND METHODS OF USE THEREOF

(71) Applicants: Florida Atlantic University Board of Trustees, Boca Raton, FL (US); University of Florida Research Foundation, Gainesville, FL (US)

(72) Inventors: Predrag Cudic, Boca Raton, FL (US); Jay McLaughlin, Gainesville, FL (US)

(73) Assignees: FLORIDA ATLANTIC UNIVERSITY RESEARCH CORPORATION, Boca Raton, FL (US); UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 173 days.

(21) Appl. No.: 16/257,580

(22) Filed: Jan. 25, 2019

(65) Prior Publication Data
US 2019/0300571 A1 Oct. 3, 2019

Related U.S. Application Data

(60) Provisional application No. 62/649,290, filed on Mar. 28, 2018.

(51) Int. Cl.
| | | |
|---|---|---|
| *A61K 31/4045* | (2006.01) |
| *A61K 47/64* | (2017.01) |
| *A61K 47/65* | (2017.01) |
| *A61K 9/00* | (2006.01) |
| *A61P 25/04* | (2006.01) |
| *A61P 25/06* | (2006.01) |
| *A61P 25/16* | (2006.01) |
| *A61P 25/18* | (2006.01) |
| *A61P 25/28* | (2006.01) |
| *A61P 25/36* | (2006.01) |
| *C07K 5/12* | (2006.01) |
| *C07K 7/64* | (2006.01) |
| *A61K 38/00* | (2006.01) |
| *C40B 40/10* | (2006.01) |

(52) U.S. Cl.
CPC .............. *C07K 5/12* (2013.01); *A61K 9/0043* (2013.01); *A61K 31/4045* (2013.01); *A61K 47/64* (2017.08); *A61K 47/65* (2017.08); *A61P 25/04* (2018.01); *A61P 25/06* (2018.01); *A61P 25/16* (2018.01); *A61P 25/18* (2018.01); *A61P 25/28* (2018.01); *A61P 25/36* (2018.01); *C07K 7/64* (2013.01); *A61K 38/00* (2013.01); *C40B 40/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,507,875 B2 * | 3/2009 | Bloksberg | ............ | C07K 14/415 800/278 |
| 7,745,391 B2 * | 6/2010 | Mintz | ..................... | A61P 31/00 514/19.3 |
| 8,067,671 B2 * | 11/2011 | Boukharov | ......... | C12N 15/8285 800/285 |
| 9,012,723 B2 * | 4/2015 | Guo | .................... | C12N 15/8261 800/285 |
| 10,611,798 B2 * | 4/2020 | Bar-Shavit | ............... | C07K 7/08 |
| 2018/0222940 A1 | 8/2018 | Zadina et al. | | |

OTHER PUBLICATIONS

Oluigbo et al., IEEE Reviews in Biomedical Engineering, vol. 5, 2012, 88-99. (Year: 2012).*
Zealand Pharma A/S, What are peptides, at URL www.zealandpharma.com/what-are-peptides, accessed May 7, 2021. (Year: 2021).*
Benavente, "Cell surface glycan-lectin interactions for biomedical applications," PhD Thesis dissertation, Florida Atlantic University, 2015—accessed at URL fau.digital.flvc.org/islandora/object/fau%3A31323. (Year: 2015).*
Wu et al, "A novel small Odorranalectin-bearing cubosomes: Preparation, brain delivery and pharmacodynamic study on amyloid-b25-35-treated rats following intranasal administration," European Journal of Pharmaceutics and Biopharmaceutics 80: 368-378 (2012) (Year: 2012).*
Shaw et al., "Tryptophan and 5-Hydroxytryptophan for depression." Cochrane Database of Systematic Reviews Iss. 1, pp. 1-18 (2010) (Year: 2010).*
Mollica et al., "Rational Approach to the Design of Bioactive Peptidomimetics: Recent Developments in Opioid Agonist Peptides," Natural Products Chemistry 46:27-61 (2015) (Year: 2015).*
Schiller et al., "Differential stereochemical requirements of mu vs. delta opioid receptors for ligand binding and signal transduction: Development of a class of potent and highly delta-selective peptide antagonists", Proceedings of the National Academy of Sciences of the United States of America, Dec. 1992, vol. 89, pp. 11871-11875.
Wen et al., "Odorranalectin-conjugated nanoparticles: Preparation, brain delivery and pharmacodynamic study on Parkinson's disease following intranasal administration", Journal of Controlled Release, Feb. 2011, vol. 151, pp. 131-138.

(Continued)

*Primary Examiner* — Julie Ha
*Assistant Examiner* — Kristina M Hellman
(74) *Attorney, Agent, or Firm* — Fox Rothschild LLP

(57) ABSTRACT

Novel cyclic peptides, cyclic peptide conjugates and compositions containing them for treating neurological diseases in a subject include an Odorranalectin (OL) sequence or modified OL sequence as a scaffold and a biologically active peptide or protein and/or therapeutic agent conjugated thereto. Methods of treatment of neurological diseases are based on intranasal delivery of a cyclic peptide or cyclic peptide conjugate as described herein. Combinatorial libraries that include a plurality of cyclic peptides have also been developed and can be used to screen for a ligand(s) for a receptor of interest.

23 Claims, 20 Drawing Sheets

Specification includes a Sequence Listing.

(56) References Cited

OTHER PUBLICATIONS

Gianolio et al., "Hyaluronan-Tethered Opioid Depots: Synthetic Strategies and Release Kinetics In Vitro and In Vivo", Bioconjugate Chemistry, Jul. 2008, vol. 19, pp. 1767-1774.

Schiller et al., "The TIPP Opioid Peptide Family: Development of delta Antagonists, delta Agonists, and Mixed mu Agonist/delta Antagonists", Biopolymers (Peptide Science), 1999, vol. 51, pp. 411-425.

Li et al., "Odorranalectin Is a Small Peptide Lectin with Potential for Drug Delivery and Targeting", PLoS One, Jun. 2008, vol. 3, No. 6, pp. 1-10.

Tang et al., ""Click" reactions: a versatile toolbox for the synthesis of peptide-conjugates", Chemical Society Reviews, Jul. 2014, vol. 43, No. 20, pp. 7013-7039.

* cited by examiner

Y$^1$A$^2$S$^3$P$^4$K$^5$-cyclo[C$^6$F$^7$R$^8$H$^9$F$^{10}$P$^{11}$V$^{12}$N$^{13}$L$^{14}$A$^{15}$C$^{16}$]T$^{17}$

SEQUENCE LISTING

```
<160> NUMBER OF SEQ ID NOS: 21

<210> SEQ ID NO 1
<211> LENGTH: 17
<212> TYPE: PRT
<213> ORGANISM: Unknown
<220> FEATURE:
<223> OTHER INFORMATION: Description of Unknown:
      Odorranalectin sequence

<400> SEQUENCE: 1

Tyr Ala Ser Pro Lys Cys Phe Arg Tyr Pro Asn Gly Val Leu Ala Cys
1               5                   10                  15

Thr

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 1,2,3,4-tetrahydroisoquinoline-3-carboxylic
      acid

<400> SEQUENCE: 2

Tyr Xaa Phe Phe
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Pro Trp Phe
1

<210> SEQ ID NO 4
<211> LENGTH: 4
<212> TYPE: PRT
<213> ORGANISM: Unknown
<220> FEATURE:
<223> OTHER INFORMATION: Description of Unknown:
      Odorranalectin sequence

<400> SEQUENCE: 4

Tyr Ala Ser Pro
1

<210> SEQ ID NO 5
```

```
<211> LENGTH: 5
<212> TYPE: PRT
<213> ORGANISM: Unknown
<220> FEATURE:
<223> OTHER INFORMATION: Description of Unknown:
      Odorranalectin sequence

<400> SEQUENCE: 5

Tyr Pro Asn Gly Val
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (7)..(7)
<223> OTHER INFORMATION: Any basic amino acid
<220> FEATURE:
<221> NAME/KEY: MOD_RES
<222> LOCATION: (8)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 6

Xaa Xaa Xaa Lys Cys Phe Xaa Xaa Xaa Xaa Xaa Xaa Xaa Xaa Cys Thr
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 1,2,3,4-tetrahydroisoquinoline-3-carboxylic
      acid

<400> SEQUENCE: 7

Tyr Pro Trp Phe Lys Cys Phe Arg Tyr Xaa Phe Phe Val Leu Ala Cys
1               5                   10                  15

Thr

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Ala
<220> FEATURE:
<221> NAME/KEY: MOD_RES
<222> LOCATION: (13)..(13)
<223> OTHER INFORMATION: D-Leu
```

<400> SEQUENCE: 8

Tyr Ala Ser Pro Lys Cys Phe Arg Tyr Ala Gly Phe Leu Leu Ala Cys
1               5                   10                  15

Thr

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: D-Leu

<400> SEQUENCE: 9

Tyr Ala Gly Phe Leu Lys Cys Phe Arg Tyr Pro Asn Gly Val Leu Ala
1               5                   10                  15

Cys Thr

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 1,2,3,4-tetrahydroisoquinoline-3-carboxylic
      acid

<400> SEQUENCE: 10

Tyr Ala Ser Pro Lys Cys Phe Arg Tyr Xaa Phe Phe Val Leu Ala Cys
1               5                   10                  15

Thr

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ala Ser Pro Lys Cys Phe Arg Gly Phe Trp Pro Lys Leu Ala Cys
1               5                   10                  15

Thr

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Ala Ser Pro Lys Cys Phe Arg His Phe Pro Val Asn Leu Ala Cys
1               5                   10                  15

Thr

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-Hydroxytryptophan

<400> SEQUENCE: 13

Trp Ala Ser Pro Lys Cys Phe Arg Gly Phe Trp Pro Lys Leu Ala Cys
1               5                   10                  15

Thr

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-Hydroxytryptophan

<400> SEQUENCE: 14

Trp Ala Ser Pro
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Trp Pro Lys
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present
<220> FEATURE:
<221> NAME/KEY: MISC_FEATURE
<222> LOCATION: (1)..(17)
<223> OTHER INFORMATION: The residues in this sequence may or may not be
      L-amino acids, D-amino acids, nonproteinogenic amino acids,
      proteinogenic amino acids, peptidomimetics, or a mix thereof.
<220> FEATURE:

<223> OTHER INFORMATION: See specification as filed for detailed
      description of substitutions and preferred embodiments

<400> SEQUENCE: 16

Xaa Ala Ser Pro Lys Cys Phe Arg Tyr Pro Asn Gly Val Leu Ala Cys
1               5                   10                  15
Thr

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ala Ser Pro Lys Cys Phe Arg Tyr Pro Asn Gly Val Leu Ala Cys
1               5                   10                  15
Thr

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(13)
<223> OTHER INFORMATION: Any amino acid
<220> FEATURE:
<221> NAME/KEY: MISC_FEATURE
<222> LOCATION: (9)..(13)
<223> OTHER INFORMATION: This region is a mixture of D-amino acids and
      L-amino acids. These amino acids can be naturally occurring amino
      acids, non-naturally occurring (synthetic) amino acids, or a mix
      thereof.
<220> FEATURE:
<223> OTHER INFORMATION: See specification as filed for detailed
      description of substitutions and preferred embodiments

<400> SEQUENCE: 18

Tyr Ala Ser Pro Lys Cys Phe Arg Xaa Xaa Xaa Xaa Xaa Leu Ala Cys
1               5                   10                  15
Thr

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Val Phe Ser Leu Cys Asn Ala Thr Tyr Pro Tyr Lys Gly Ala Cys
1               5                   10                  15
Pro

<210> SEQ ID NO 20
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 20

Cys Ala Ser Pro Lys Cys Phe Arg Tyr Pro Asn Gly Val Leu Ala Cys
1               5                   10                  15
Thr

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ser Pro Lys Cys Phe Arg Tyr Pro Asn Gly Val Leu Ala Cys Thr
1               5                   10                  15
```

CYCLIC PEPTIDES, CYCLIC PEPTIDE CONJUGATES AND METHODS OF USE THEREOF

CROSS-REFERENCE TO RELATED APPLICATION

This application claims priority to U.S. Provisional Application No. 62/649,290 filed Mar. 28, 2018, which is herein incorporated by reference in its entirety.

STATEMENT REGARDING FEDERALLY SPONSORED RESEARCH

This invention was made with government support under grant no. 1 R21 DA039722-01A1 awarded by the National Institutes of Health/National Institute on Drug Abuse. The government has certain rights in the invention.

FIELD OF THE INVENTION

The invention relates generally to the fields of medicine and drug discovery. In particular, the invention relates to cyclic peptides, cyclic peptide conjugates and compositions including same that are administered intranasally for delivery to the brain and treatment of neurological diseases, neurological disorders and disabling neurological conditions.

REFERENCE TO A SEQUENCE LISTING

This application includes a "Sequence Listing" which is provided as an electronic document having the file name "6818-309-1_ST25.txt" (7,688 bytes, created Jan. 25, 2019), which is herein incorporated by reference in its entirety.

BACKGROUND

Brain and central nervous system (CNS) diseases are leading causes of disability worldwide, accounting for significant hospitalization and prolonged care. Treatment for these diseases remains challenging due to the inability of many therapeutic agents, especially hydrophobic and large molecular weight drugs, to cross the blood-brain barrier (BBB) and blood-cerebrospinal fluid barrier (BCB). Direct delivery of therapeutics from the nasal cavity into the brain (intranasal (i.n.) delivery) bypasses the BBB and BCB, providing an alternative route to invasive methods of drug administration (Bitter et al. Curr Probl Dermatol 2011, 40, 20-35; Pardeshi C. V. & Belgamwar V. S., Expert Opin Drug Deliv 2013, 10 (7), 957-72; Frey, W. H. n., Drug Deliv. Techn. 2002, 2, 46-49). A few therapeutic agents, including peptides and proteins otherwise impermeable to the BBB and BCB, have been delivered to the brain via this route (Lalatsa et al., Mol Pharm 2014, 11 (4), 1081-93; Illum, L., J Control Release 2003, 87 (1-3), 187-98). However, drug hydrophobicity, molecular weight and degree of ionization affect the drug transport into the brain after intranasal administration.

Intranasal delivery exploits the olfactory or trigeminal cranial nerve systems which initiate in the brain and terminate in the nasal cavity at the olfactory neuroepithelium or respiratory epithelium. CNS targeting action can be achieved due to direct transport of a drug from the submucosal space of the nose into the cerebrospinal fluid (CSF) compartment of the brain, avoiding systemic circulation of the drug, and reducing the risk of systemic side effects as well as hepatic/renal clearing. However, intranasal-CSF administration has limitations, including gradual elimination of the drug from the CSF into the blood due to the normal replacement of the CSF (four to five times daily), and the logarithmic decrease of brain penetration by drug with distance from the CSF surface. Using current methods, the quantities of drug administered intranasally that are transported directly from nose-to-brain are very low, typically less than 0.1%. To improve i.n. drug delivery to the brain, two main approaches have been utilized: (a) modification of nasal membrane permeability by employment of absorption enhancers, such as surfactants, bile salts, fatty acids and polymeric enhancers (Davis, S. & S. Illum, L., Clin Pharmacokinet 2003, 42 (13), 1107-28; Duan, X. & Mao, S., Drug Discov Today 2010, 15 (11-12), 416-27) and (b) use of nanoparticle systems that can carry drugs across the mucosal barrier and protect drugs from degradation in the nasal cavity (Ali et al., Curr Pharm Des 2010, 16 (14), 1644-53; Illum L., J Pharm Sci 2007, 96 (3), 473-83; Mistry et al., Int J Pharm 2009, 379 (1), 146-57). However, these approaches each possess shortcomings. In the case of absorption-enhancing molecules, local or systemic intolerance after inhalation and membrane damage produced by many enhancers represent major limitations. Moreover, suboptimal delivery due to limited transmucosal transfer of nanoparticles, slow drug release (which limits bioavailability), and short residence time in the nasal cavity (due to mucociliary clearance) are limitations typically associated with nanoparticles.

The challenge remains to improve the transfer efficiency of the drug from the olfactory epithelium to the brain, in order to safely, predictably and successfully reach therapeutically-relevant drug levels in the targeted brain regions. Therefore, the development of novel strategies that effectively deliver therapeutic agents into the brain is of great importance.

SUMMARY

Described herein are novel cyclic peptides, cyclic peptide conjugates, compositions, kits and methods that address the need for effective intranasal delivery to the brain of therapeutic agents such as peptides, proteins, small molecules and nanoparticles. They can be administered to a subject having a neurological disease, disorder, or disabling condition (e.g., schizophrenia, meningitis, migraine, Parkinson's, Alzheimer's disease, pain, addiction, overdose etc.) for treatment of the neurological disease, disorder or disabling condition. They can be administered to a subject having more than one neurological disease, disorder or disabling condition. The cyclic peptides and cyclic peptide conjugates are based on a novel strategy of grafting (inserting) a biologically active peptide within and/or conjugating (joining together) protein or small molecule onto the scaffold of a cyclic peptide that exhibits bio-adhesive properties, in particular, specific binding to cells of the olfactory epithelium of nasal mucosa. The permeability of nasal mucosa to a variety of compounds, including very large and polar molecules, contributes to the unexpected success of this novel delivery method. The cyclic peptides and cyclic peptide conjugates described herein include an Odorranalectin (OL) sequence or modified OL sequence as a scaffold. OL is a 17-amino acid cyclic peptide having the sequence $Y^1A^2S^3P^4K^5$-cyclo$[C^6F^7R^8Y^9P^{10}N^{11}G^{12}V^{13}L^{14}A^{15}C^{16}]T^{17}$ (SEQ ID NO:1), that exhibits lectin-like properties, and that can specifically bind to L-fucose, which is widely distributed on the olfactory epithelium of nasal mucosa. The novel strategy for improved i.n. delivery of therapeutic agents (e.g., pharmaceutically relevant bioactive peptides) to the brain is based on: a) exploitation of a high abundance of L-fucose on olfactory cells for extending the residence time of a biologically active peptide or protein in the nasal cavity, and b) grafting or conjugating of the biologically active protein or peptide sequence into or to the scaffold of fucose-binding OL with nose-to-brain homing capability. The L-fucose binding site in OL consists of only five amino acids, $Lys^5$, $Cys^6$, $Phe^7$, $Cys^{16}$ and $Thr^{17}$. Therefore, modification of the OL amino acid sequence that is not directly involved in fucose binding provides novel and unique analogs with desired therapeutic activity and preserved fucose affinity for successful nose-to-brain delivery. In some embodiments of a cyclic peptide conjugate as described herein, a small molecule is attached (conjugated) directly or indirectly to OL or an OL analogue.

It was discovered that a biologically active peptide (an opioid receptor ligand) could be grafted into and/or conjugated to an OL sequence and that the resultant cyclic peptide, after i.n. administration, was delivered to a mammalian brain where the biologically active peptide retained its functional activity. The experimental results described herein also demonstrate the ability of a combinatorial library that includes a plurality of cyclic peptides as described herein to identify ligands for receptors of interest. Based on these experimental results, the cyclic peptides and cyclic peptide conjugates described herein may be delivered via intranasal delivery for treating neurologic diseases, neurologic disorders, and disabling neurologic conditions, and may be used to screen for a ligand(s) for a receptor of interest.

Accordingly, described herein is a cyclic peptide of the general Formula I:

(SEQ ID NO: 6)
$(X)_m$-Lys-*cyclo*[Cys-Phe-$X_1$ - $X_2$ - $X_3$ - Cys]-Thr wherein:

X is an amino acid sequence having a length of m amino acids, $X_1$ is a basic amino acid, $X_2$ is an amino acid sequence having a length of 5 amino acids, $X_3$ is an amino acid sequence having a length of 2 amino acids, wherein m is at least 3, and wherein at least one of $(X)_m$ and $X_2$ includes a biologically active peptide or protein, or a pharmaceutically acceptable salt thereof. In one embodiment of the cyclic peptide, the biologically active peptide or protein is an opioid receptor ligand or analogue thereof. For example, the opioid receptor ligand can be a δ opioid receptor (DOR) antagonist, a DOR agonist, a μ opioid receptor (MOR) antagonist, a MOR agonist, a κ opioid receptor (KOR) antagonist, or a KOR agonist. In one embodiment of the cyclic peptide, $(X)_m$ is an opioid receptor ligand or analogue thereof. In one embodiment of the cyclic peptide, $X_2$ includes an opioid receptor ligand or analogue thereof. In such embodiments, typically the cyclic peptide modulates opioid receptor activity. A cyclic peptide can include one of the following amino acid sequences:

(SEQ ID NO: 8)
DADLE-OL = $Y^1A^2S^3P^4K^5$-*cyclo*[$C^6F^7R^8Y^9a^{10}G^{11}F^{12}I^{13}$
$L^{14}A^{15}C^{16}$]$T^{17}$;

-continued (SEQ ID NO: 9)
DADLE-OL II = $Y^1a^2G^3F^4I^5K^6$-*cyclo*[$C^7F^8R^9Y^{10}P^{11}N^{12}$
$G^{13}V^{14}L^{15}A^{16}C^{17}$]$T^{18}$;

(SEQ ID NO: 10)
TIPP-OL = $Y^1A^2S^3P^4K^5$-*cyclo*[$C^6F^7R^8Y^9Tic^{10}F^{11}F^{12}V^{13}$
$L^{14}A^{15}C^{16}$]$T^{17}$;

(SEQ ID NO: 7)
TIPP-EM1-OL. = $Y^1P^2W^3F^4K^5$-*cyclo*[$C^6F^7R^8Y^9Tic^{10}F^{11}$
$F^{12}V^{13}L^{14}A^{15}C^{16}$]$T^{17}$;

(SEQ ID NO: 11)
OLKOR-L1 = $Y^1A^2S^3P^4K^5$-*cyclo*[$C^6F^7R^8G^9F^{10}W^{11}P^{12}K^{13}$
$L^{14}A^{15}C^{16}$]$T^{17}$;
and (SEQ ID NO: 12)
OLMOR-L1 = $Y^1A^2S^3P^4K^5$-*cyclo*[$C^6F^7R^8H^9F^{10}P^{11}V^{12}N^{13}$
$L^{14}A^{15}C^{16}$]$^{17}$, wherein a=D-Ala and 1=D-Leu.

In some embodiment, the cyclic peptide further includes a therapeutic agent conjugated to $(X)_m$. In some embodiments of a cyclic peptide, the therapeutic agent is a small molecule, and in another embodiment, the therapeutic agent is a protein (e.g., growth hormone). In one embodiment, the therapeutic agent is an opioid receptor ligand or analogue thereof (e.g., a DOR antagonist, a DOR agonist, a MOR antagonist a MOR agonist, a KOR antagonist, or a KOR agonist). Examples of therapeutic agents include analgesic, anti-convulsant, antidote, anti-microbial, anti-cancer, anti-inflammatory, and anti-neurodegenerative. Examples of small molecules include 5HTrp, naloxone, serotonin, dopamine, L-DOPA, epinephrine, norepinephrine, histamine, adenosine triphosphate, adenosine, cannabidiol (CBD), CBD derivative, tetrahydrocannabinol (THC), THC derivative, nabilone, selective serotonin reuptake inhibitor, fluvoxamine, serotonin-norepinephrine reuptake inhibitor (SNRI), desvenlafaxine, milnacipran, levomilnacipran, memantine, and pramipexole. In one embodiment, the cyclic peptide includes the amino acid sequence: OLKOR-L1-5HTrp=5-$HTrp^1$-$A^2S^3P^4K^5$-cyclo [$C^6F^7R^8G^9F^{10}W^{11}P^{12}K^{13}L^{14}A^{15}C^{16}$]$T^{17}$ (SEQ ID NO: 13).

Also described herein is a cyclic peptide conjugate including a cyclic peptide having conjugated to its N-terminus a therapeutic agent, the cyclic peptide including the amino acid sequence:

(SEQ ID NO: 16)
$(X)_m$-$A^2S^3P^4K^5$-*cyclo*[$C^6F^7R^8Y^9P^{10}N^{11}G^{12}V^{13}L^{14}A^{15}C^{16}$]
$T^{17}$, wherein X is a linker, or an amino acid sequence at the N-terminus having a length of m amino acids, wherein m is 0 or at least 1, and wherein the amino acids are L-amino acids, D-amino acids, or a combination thereof, or a pharmaceutically acceptable salt thereof. In the cyclic peptide, the therapeutic agent can be conjugated to the N-terminus of the cyclic peptide by a cleavable bond or linker. In another embodiment, the therapeutic agent is conjugated directly to the N-terminus of the cyclic peptide. The therapeutic agent can be a small molecule, e.g., 5HTrp, naloxone, serotonin, dopamine, L-DOPA, epinephrine, norepinephrine, histamine, adenosine triphosphate, adenosine, cannabidiol (CBD), CBD derivative, tetrahydrocannabinol (THC), THC derivative, nabilone, selective serotonin reuptake inhibitor, fluvoxamine, serotonin-norepinephrine reuptake inhibitor (SNRI), desvenlafaxine, milnacipran, levomilnacipran, memantine, pramipexole, etc. In one embodiment, the cyclic peptide conjugate has the sequence:

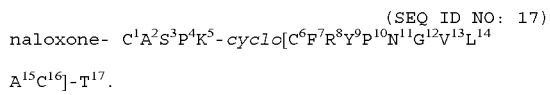

(SEQ ID NO: 17)
naloxone- $C^1A^2S^3P^4K^5$-cyclo$[C^6F^7R^8Y^9P^{10}N^{11}G^{12}V^{13}L^{14}A^{15}C^{16}]$-$T^{17}$.

Further described herein is a composition including a pharmaceutically acceptable carrier and a therapeutically effective amount of a cyclic peptide of the general Formula I, or a cyclic peptide conjugate including a cyclic peptide having conjugated to its N-terminus a therapeutic agent, the cyclic peptide comprising the amino acid sequence:

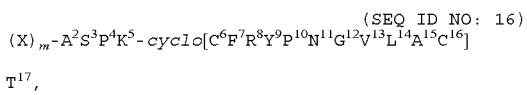

(SEQ ID NO: 16)
$(X)_m$-$A^2S^3P^4K^5$-cyclo$[C^6F^7R^8Y^9P^{10}N^{11}G^{12}V^{13}L^{14}A^{15}C^{16}]$ $T^{17}$, wherein X is a linker, or an amino acid sequence at the N-terminus having a length of m amino acids, wherein m is 0 or at least 1, and wherein the amino acids are L-amino acids, D-amino acids, or a combination thereof, or a pharmaceutically acceptable salt thereof. In one embodiment of the composition, the biologically active peptide or protein is an opioid receptor ligand or analogue thereof.

Still further described herein is a combinatorial library including a plurality of cyclic peptides of the general Formula II:

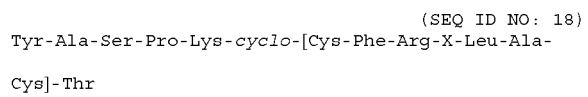

(SEQ ID NO: 18)
Tyr-Ala-Ser-Pro-Lys-cyclo-[Cys-Phe-Arg-X-Leu-Ala-Cys]-Thr wherein: X is an amino acid sequence having a length of 5 amino acids and includes D-amino acids, L-amino acids, non-natural synthetic amino acids, naturally occurring amino acids, or a mixture thereof, wherein at least a portion of the cyclic peptides have an affinity for at least one opioid receptor and ability to modulate activity of the at least one opioid receptor.

Additionally described herein is a combinatorial library that includes a plurality of cyclic peptides of the general Formula I.

In some embodiments of the combinatorial libraries described herein, the at least one opioid receptor is one or more of: MOR, KOR and DOR.

Yet further described herein is a method of identifying opioid cyclic peptides. The method includes screening a combinatorial library as described herein in at least one assay.

Still further described herein is a method of treating a neurological disorder, neurological disease or disabling neurological condition in an individual (e.g., a human). The method includes administering to the individual a composition as described herein via intranasal delivery to the individual's brain. In the method, the neurological disease, neurological disorder and disabling neurological condition can be any neurological disease, neurological disorder or disabling neurological condition, e.g., one or more of schizophrenia, meningitis, migraine, Parkinson's, Alzheimer's disease, pain, overdose and addiction.

"Neurological disease", "neurological disorder" and "disabling neurological condition" as used herein may be any type of diseases or disorder or disabling condition of the brain, spine and the nerves that connect them including but not limited to, as examples, schizophrenia, meningitis, migraine, Parkinson's, Alzheimer's disease, chronic pain and addiction.

The terms "agent" and "therapeutic agent" as used herein refer to a chemical entity or biological product, or combination of chemical entities or biological products, administered to a subject to diagnose and/or treat a disease or condition (e.g., neurological disease). Examples of agents include small molecules, nanoparticles, drugs and biologics (e.g., peptides, proteins, etc.).

By the phrase "biologically active peptide or protein" is meant any peptide or protein that exhibits a direct or indirect effect (e.g., a beneficial effect, an adverse effect) on living matter (e.g., a cell, cells, organelle, tissue, etc.). Examples of biologically active peptides or proteins include receptors, proteins, and enzymes present in the CNS.

As used herein, the term "small molecule" means any organic compound with a molecular weight below 900 Daltons that affects a biologic process.

The term "cyclic peptide" as used herein means a peptide chain possessing cyclic ring structure. The ring structure can be formed by linking one end of the peptide to the other with an amide bond, or other chemically stable bonds such as lactone, ether, thioether, disulfide, etc.

By the term "opioid cyclic peptide" is meant any cyclic peptide that has an affinity for at least one opioid receptor and is able to modulate activity (e.g, activate or block activity) of the at least one opioid receptor(s).

As used herein, the terms "conjugated to" and "conjugate to" mean when one molecule or agent is physically or chemically coupled or adhered or attached to or incorporated into another molecule or agent and encompass the terms "grafted" and "grafting" as used herein. Typically "grafted" means "inserted" and refers to short peptide sequences (e.g. enkephalins such as DADLE) that can be inserted into the OL scaffold by replacing part of the original (naturally occurring) OL sequence. Rather than being inserted (grafted) into the OL scaffold, large biomolecules and small molecule drugs are conjugated to the OL scaffold. Examples of conjugation include covalent linkage (e.g., covalently bound drug or other small molecule), linkage via cleavable bond/linker (e.g., amide (peptide) bond, ester bond, thioester bond, oxyme bond, hydrazone bond, disulfide bond, hydrazine bond etc.)

The terms "group," "functional group," "moiety," "molecular moiety," or the like are somewhat synonymous in the chemical arts and are used to refer to distinct, definable portions or units of a molecule, and to units that perform some function or activity and are reactive with other molecules or portions of molecules. In the cyclic peptides and cyclic peptide conjugates described herein, a small molecule generally has at least one functional group (e.g., thiol, hydroxyl, amino, carboxyl, etc.) that is suitable for attachment (conjugation) directly to a cyclic peptide as described herein, e.g., via a linker to the cyclic peptide.

By the terms "modulate" and "modulates" is meant to increase or decrease. These terms can refer to increasing or decreasing an activity, level or function of a molecule (e.g., an opioid receptor), or effecting a change with respect to one or more biological or physiological mechanisms, effects, responses, functions, pathways or activities in which, for example, activity of a receptor (e.g., a CNS receptor) is involved.

The terms "patient," "subject" and "individual" are used interchangeably herein, and mean a subject to be treated, diagnosed, and/or to obtain a biological sample from. Subjects include, but are not limited to, humans, non-human primates, horses, cows, sheep, pigs, rats, mice, dogs, and cats. A human in need of treatment for a neurological disease, disorder or disabling neurological condition is an example of a subject.

As used herein, the terms "treatment" and "therapy" are defined as the application or administration of a therapeutic agent or therapeutic agents to a patient, or application or administration of the therapeutic agent to an isolated tissue or cell line from a patient, who has a disease or disorder or condition, a symptom of disease or disorder or condition or a predisposition toward a disease or disorder or condition, with the purpose to cure, heal, alleviate, relieve, alter, remedy, ameliorate, improve or affect the disease, the symptoms of disease or disorder or condition, or the predisposition toward disease or disorder or condition.

Although cyclic peptides, cyclic peptide conjugates, compositions, kits, and methods similar or equivalent to those described herein can be used in the practice or testing of the present invention, suitable cyclic peptides, cyclic peptide conjugates, compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 13A is a dose response of OLKOR-L1-5OHTrp. Antinociceptive effects were observed 2 minutes after i.n. administration. FIG. 13B shows a significant increase in antinociceptive activity observed for OLKOR-L1-5HTrp. FIG. 13C shows more potent and longer lasting antiallodynic effects observed for OLKOR-L1-5HTrp in the mouse chronic constriction injury (CCI) model of neuropathic pain compared to morphine.

DETAILED DESCRIPTION

Figure 1:
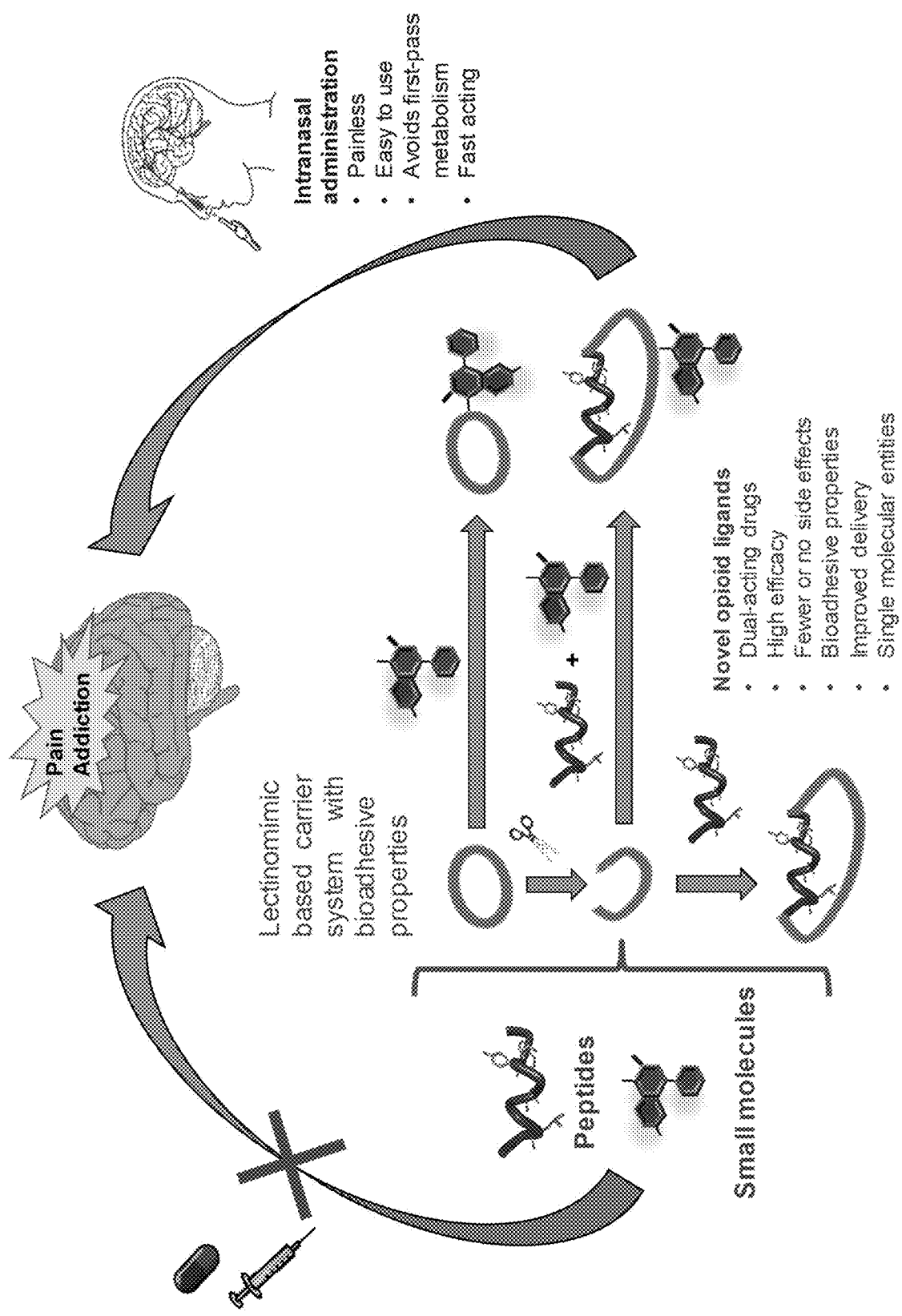
FIG. 1 is an illustration of a typical embodiment of cyclic peptide-based drug delivery to the brain.
Figure 2:
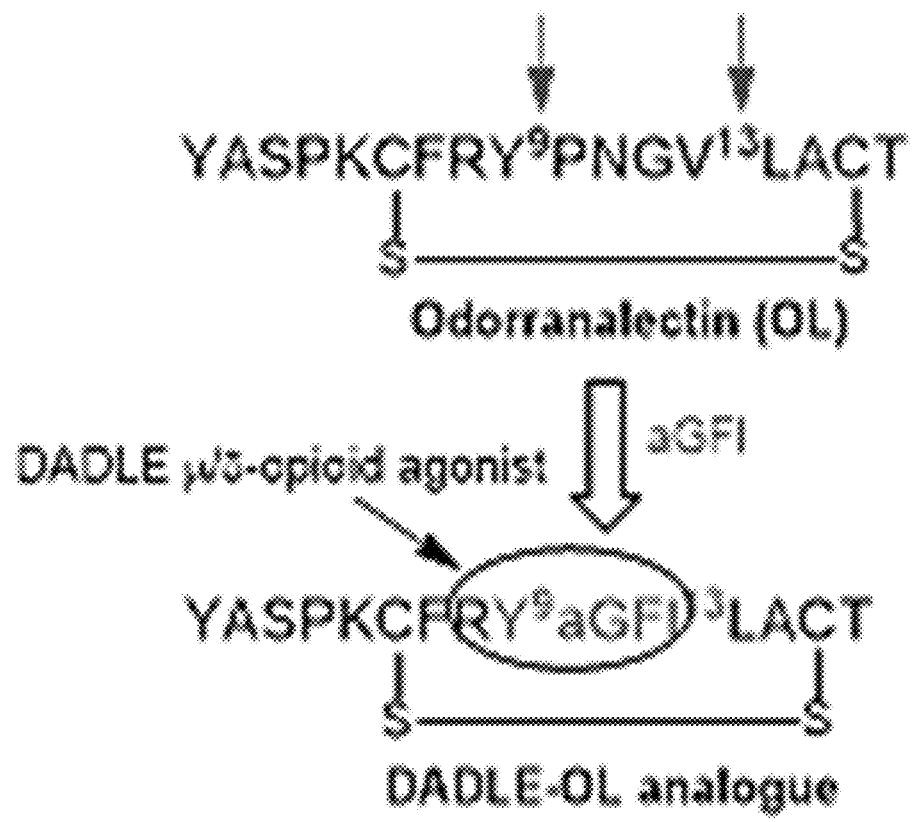
FIG. 2 shows grafting of DADLE sequence into the OL scaffold yielding a novel cyclic opioid peptide. The top sequence is SEQ ID NO:1 and the bottom sequence is SEQ ID NO: 8.

Novel cyclic peptides and cyclic peptide conjugates and compositions containing them, as well as methods of using them, are described herein. A novel therapy has been developed for the treatment of neurological diseases, disorders, and disabling conditions based on the intranasal delivery of a cyclic peptide or cyclic peptide conjugate as described herein. Combinatorial libraries that include a plurality of cyclic peptides have also been developed and can be used to screen for a ligand(s) for a receptor of interest. The experimental results described in more detail in the Examples below demonstrate the therapeutic utility of the cyclic peptides and cyclic peptide conjugates that are delivered intransally (i.n.) for treating neurologic diseases, disorders and conditions such as addiction, for example. A known δ opioid receptor ligand (DOR), D-Ala-D-Leu enkephalin (DADLE), was grafted (inserted) into an OL scaffold and it was demonstrated that the novel DADLE-OL cyclic peptide retains the properties of both parent peptides (the DADLE and the OL), including opioid receptor ligand functional activity. To demonstrate suitability of an OL scaffold for additional structural modifications, OL analogues differing in the position and sequences of the grafted opioid peptide ligands were synthesized and their in vivo activity was assessed. It was shown that the additional OL analogues can be delivered via the intranasal route to the mouse brain and produce biological effects in the brain in a concentration-dependent manner. To identify novel opioid ligands based on the OL scaffold, a focused positional-scanning synthetic combinatorial library (PSCL) of 2,476,099 cyclic peptides was prepared and screened for affinity for μ, δ and κ opioid receptors, from which novel OL-based ligands were identified. These data demonstrate the feasibility of the molecular grafting approach for the design of novel OL analogs for direct nose-to-brain delivery of therapeutic peptides, proteins, small molecules and other therapeutic agents without undesirable side effects. They also demonstrate the utility of cyclic peptide combinatorial libraries for screening for and identifying therapeutic agents (e.g., receptor ligands). The described strategy has broad implications for the development of novel drugs and delivery carriers for brain targeting and the treatment of neurological diseases, disorders and disabling conditions.

Cyclic Peptides, Cyclic Peptide Conjugates, and Compositions for Treating Neurological Diseases, Disorders and Disabling Conditions The cyclic peptides, cyclic peptide conjugates and compositions described herein are capable of traveling to an individual's brain via intranasal delivery and exerting a biological effect in the CNS. The cyclic peptides include a biologically active peptide or protein and/or other therapeutic agent (e.g., a small molecule) and an OL sequence or modified OL sequence. OL can be modified at its N-terminus (amino acids Tyr-Ala-Ser-Pro (SEQ ID NO: 4) which are amino acids 1-4 of SEQ ID NO:1) and at its β-turn region (amino acids Tyr-Pro-Asn-Gly-Val (SEQ ID NO: 5) which are amino acids 9-13 of SEQ ID NO:1), but not at its bioadhesive domain (amino acids 5-7, 16 and 17 of SEQ ID NO:1). Examples of chemical modifications at its N-terminus include: insertion of peptide sequences composed of L-, D- and nonproteinogenic amino acids; insertion of peptidomimetics; conjugation of small molecules; conjugation of proteins; and conjugation of nanoparticles. Examples of chemical modifications at OL's β-turn region include: insertion of peptide sequences composed of L-, D- and nonproteinogenic (synthetic) amino acids; and insertion of peptidomimetics.

In one embodiment, a cyclic peptide has the general Formula 1:

$(X)_m$-Lys-cyclo[Cys-Phe-$X_1$-$X_2$-$X_3$-Cys]-Thr    (SEQ ID NO: 6).

In this formula, X is an amino acid sequence having a length of m amino acids (m is at least 3); $X_1$ is a basic amino acid; $X_2$ is an amino acid sequence having a length of 5 amino acids; $X_3$ is an amino acid sequence having a length of 2 amino acids; and at least one of $(X)_m$ and $X_2$ includes a biologically active peptide or protein (e.g., an opioid receptor ligand or analogue thereof). A cyclic peptide may be a pharmaceutically acceptable salt thereof. In a cyclic peptide of Formula 1, X can be any protein or peptide sequence having a length (i.e., m) of at least 3 (e.g., 3, 4, 5, 6, 7, 8, 9, 10, etc.) amino acids, but can be up to several thousand amino acids in length. For example, X can be Tyr-Ala-Ser-Pro (SEQ ID NO: 4) which are amino acids 1-4 of the naturally occurring OL sequence (SEQ ID NO:1). The amino acids of X can be L-amino acids (e.g., all L-amino acids), D-amino acids (e.g., all D-amino acids), nonproteinogenic (synthetic) amino acids, peptidomimetics, or a mix thereof. These amino acids can be naturally occurring amino acids, non-naturally occurring (synthetic) amino acids, or a mix thereof. Generally, the order and types of amino acids is determined based upon the interaction of the cyclic peptide with its biological target(s). In a cyclic peptide of Formula 1, $X_1$ can be any basic amino acid (e.g., Lys, Arg). This amino acid can be a naturally occurring amino acid or a non-naturally occurring (synthetic) amino acid. $X_1$ corresponds to position (amino acid) 8 of the naturally occurring OL sequence (SEQ ID NO: 1). In a cyclic peptide of Formula 1, $X_2$ can be any 5 amino acids, and corresponds to amino acids 9-13 of the naturally occurring OL sequence (SEQ ID NO: 1). These amino acids can be naturally occurring amino acids, non-naturally occurring (synthetic) amino acids, or a mix thereof. In a cyclic peptide of Formula 1, the amino acids of $X_3$ correspond to amino acids 14 and 15 of the naturally occurring OL sequence (SEQ ID NO: 1), and can be naturally occurring amino acids, non-naturally occurring (synthetic) amino acids, L-amino acids, D-amino acids, or a mix thereof.

The biologically active peptide or protein can be any peptide or protein that exhibits a an effect (e.g., beneficial effect, adverse effect) on living matter (e.g., a cell, cells, organelle, tissue, etc.). Examples of biologically active peptides or proteins include receptors, proteins, and enzymes present in the CNS. In a typical embodiment, the biologically active peptide or protein is a receptor, protein or enzyme present in the CNS. In some embodiments, the biologically active peptide or protein is an opioid receptor ligand or analogue thereof. In such embodiments, one or both of $(X)_m$ and $X_2$ can be an opioid receptor ligand or analogue thereof. One embodiment of a cyclic peptide in which both $(X)_m$ and $X_2$ are or include opioid receptor ligands is the cyclic peptide TIPP-EM1-OL $Y^1P^2W^3F^4K^5$-cyclo[$C^6F^7R^8Y^9Tic^{10}F^{11}F^{12}V^{13}L^{14}A^{15}C^{16}$]$T^{17}$ (SEQ ID NO: 7), a dual-acting cyclic peptide containing a MOR agonist (MOR active sequence) inserted into positions 1-4 of OL (SEQ ID NO:1) and a DOR antagonist (DOR active sequence) inserted into positions 9-12 of OL (SEQ ID NO:1). In TIPP-EM1-OL: $X_m$ is EM1; $X_1$ is Arg; $X_2$ is Tipp-Val; and $X_3$ is Leu-Ala. Generally in these embodiments, the cyclic peptide modulates activity of the opioid receptor(s). Examples of opioid receptor ligands include a δ opioid receptor (DOR) antagonist, a DOR agonist, a opioid receptor (MOR) antagonist, a MOR agonist, a κ opioid receptor (KOR) antagonist, and a KOR agonist. In the Examples below, OL-based MOR, DOR and KOR agonists and DOR antagonists were generated by modifying OL residues 1-4, 9-12, and 9-13 of SEQ ID NO:1. Opioid receptor ligands and assays involving same are described, for example, in U.S. application Ser. No. 15/145,901, incorporated herein by reference.

Examples of cyclic peptides having the general Formula I include:

(SEQ ID NO: 8)
DADLE-OL = $Y^1A^2S^3P^4K^5$-cyclo[$C^6F^7R^8Y^9a^{10}G^{11}F^{12}I^{13}$ $L^{14}A^{15}C^{16}$]$T^{17}$;

(SEQ ID NO: 9)
DADLE-OL II = $Y^1a^2G^3F^4I^5K^6$-cyclo[$C^7F^8R^9Y^{10}P^{11}N^{12}$ $G^{13}V^{14}L^{15}A^{16}C^{17}$]$T^{18}$;

(SEQ ID NO: 10)
TIPP-OL = $Y^1A^2S^3P^4K^5$-cyclo[$C^6F^7R^8Y^9Tic^{10}F^{11}F^{12}V^{13}$ $L^{14}A^{15}CIT^{16}$]$T^{17}$;

(SEQ ID NO: 7)
TIPP-EM1-OL. = $Y^1P^2W^3F^4K^5$-cyclo[$C^6F^7R^8Y^9Tic^{10}F^{11}$ $F^{12}V^{13}L^{14}A^{15}C^{16}$]$T^{17}$;

(SEQ ID NO: 11)
OLKOR-L1 = $Y^1A^2S^3P^4K^5$-cyclo[$C^6F^7R^8G^9F^{10}W^{11}P^{12}K^{13}$ $L^{14}A^{15}C^{16}$]$T^{17}$;
and (SEQ ID NO: 12)
OLMOR-L1 = $Y^1A^2S^3P^4K^5$-cyclo[$C^6F^7R^8H^9F^{10}P^{11}V^{12}N^{13}$ $L^{14}A^{15}C^{16}$]$T^{17}$, wherein a=D-Ala and l=D-Leu.

In some embodiments, a cyclic peptide of general Formula 1 further includes a therapeutic agent conjugated to $(X)_m$. Examples of therapeutic agents include analgesics, antidepressants, anticonvulsants, antidotes, antimicrobials (e.g., anti-viral agents, antibiotics), anti-cancer agents, anti-inflammatory agents, anti-neurodegenerative agents, etc. In some embodiments, the therapeutic agent is a small molecule. Any small molecule can be conjugated to a cyclic peptide of the general Formula I. Specific examples of small molecules include 5HTrp, naloxone, serotonin, dopamine, L-DOPA, epinephrine, norepinephrine, histamine, adenosine triphosphate, adenosine, cannabidiol (CBD), CBD derivative, tetrahydrocannabinol (THC), THC derivative, nabilone, selective serotonin reuptake inhibitor, fluvoxamine, serotonin-norepinephrine reuptake inhibitor (SNRI), desvenlafaxine, milnacipran, levomilnacipran, memantine, and pramipexole. One example of a cyclic peptide of general Formula I having a therapeutic agent conjugated thereto is:

(SEQ ID NO: 13)
OLKOR-L1-5HTrp = 5-HTrp$^1$-$A^2S^3P^4K^5$-cyclo[$C^6F^7R^8G^9$ $F^{10}W^{11}P^{12}K^{13}L^{14}A^{15}C^{16}$]$T^{17}$.

In this example, the therapeutic agent is the small molecule 5HTrp (a serotonin biosynthetic precursor) that was conjugated to the Ala at position 1 of SEQ ID NO: 1 by a standard solid-phase peptide synthesis protocol. In this cyclic peptide, $X_m$ is 5HTrp-Ala-Ser-Pro (SEQ ID NO: 14); $X_1$ is Arg; $X_2$ is a KOR agonist (Gly-Phe-Trp-Pro-Lys SEQ ID NO: 15); and $X_3$ is Leu-Ala. In other embodiments, the therapeutic agent is a peptide or a protein, e.g., a growth hormone or an opioid receptor ligand or analogue thereof, or a nanoparticle.

The cyclic peptide conjugates described herein are composed of a cyclic peptide having conjugated to its N-terminus a therapeutic agent. The therapeutic agent can be conjugated to the N-terminus of the cyclic peptide by any suitable means, e.g., conjugated directly to the N-terminus via a cleavable bond or linker, via "click" reactions, etc. Examples of click reactions include: Cu(I)-catalyzed azide-alkyne cycloaddition (CuAAC), strain-promoted azide-alkyne cycloaddition (SPAAC), thiol-ene reaction, thiol-Michael addition, oxime ligation, Diels-Alder reaction, and Staudinger ligation and native chemical ligation.

In a typical cyclic peptide conjugate, the cyclic peptide includes the amino acid sequence: $(X)_m$-$A^2S^3P^4K$-cyclo[$C^6F^7R^8Y^9P^{10}N^{11}G^{12}V^{13}L^{14}A^{15}C^{16}$]$T^{17}$ (SEQ ID NO: 16), wherein X is a linker, or an amino acid sequence at the N-terminus having a length of m amino acids; m is 0 or at least 1; and the amino acids are L-amino acids, D-amino acids, nonproteinogenic amino acids, proteinogenic amino acids, peptidomimetics, or a mix thereof. A cyclic peptide conjugate may be a pharmaceutically acceptable salt thereof. A specific example of such a cyclic peptide conjugate is:

naloxone-$C^1A^2S^3P^4K^5$-cyclo [$C^6F^7R^8Y^9P^{10}N^{11}G^{12}V^{13}L^{14}A^{15}C^{16}$]$T^{17}$ (SEQ ID NO: 17). In this embodiment, X is Cys and the therapeutic agent is a small molecule—naloxone—directly attached to the N-terminus of the cyclic peptide via a cleavable/bond linker. However, the therapeutic agent can be conjugated to the cyclic peptide by any suitable method, chemistry or means. In embodiments in which X is a linker, the linker can be any suitable linker, e.g., polyethylene glycol (PEG), sebacic acid, suberic acid, dithio-bis-maleimidoethane (DTME), dimethyl pimelimidate, etc. The therapeutic agent can be any agent suitable for treating a neurological disease, disorder and disabling condition (e.g., peptides, proteins, small molecules, nanoparticles). In an embodiment in which the therapeutic agent is a small molecule, as with the cyclic peptides described above, the small molecule can be any small molecule. Similarly, in an embodiment in which the therapeutic agent is a peptide or protein, any therapeutic peptide or protein can be used.

Small molecules, proteins, nanoparticles and other therapeutic agents can be conjugated to a cyclic peptide by any suitable protocol. Typically, the small molecule or other therapeutic agent is conjugated to the N-terminus of the cyclic peptide. Small molecules and other therapeutic agents can also be conjugated, for example, using known chemistries (see Wen T. and M. L. Becker, Chem. Soc. Rev., 2014, 43:p. 7013). As another example, small molecules can be conjugated via amide bond (peptide chemistry). As another example, small molecules (and other therapeutic agents) can be conjugated by "click" reactions. Different types of "click" reactions have been developed to synthesize peptide conjugates, including Cu(I) catalyzed azide-alkyne cycloaddition (CuAAC), strain promoted azide-alkyne cycloaddition (SPAAC), thiol-ene reaction, Michael addition, oxyme ligation, Diels-Alder reaction, Staudinger ligation and native chemical ligation, (Wen Tang, Matthew L. Becker, Chem. Soc. Rev., 2014, 43, 7013-7039). In some embodiments, the N-terminal part of OL possessing a preselected functional group(s) suitable for the above mentioned "click" reaction is selected as a place for conjugation. The main limitation of the "click" reactions for the small molecule conjugation to peptide is that the desired functional groups must be compatible with the reaction conditions for peptide coupling, deprotection and cleavage. Alternatively, if the small molecule (or other therapeutic agent) possesses the amino or carboxyl functional groups, standard peptide coupling reactions can be used.

Figure 14:
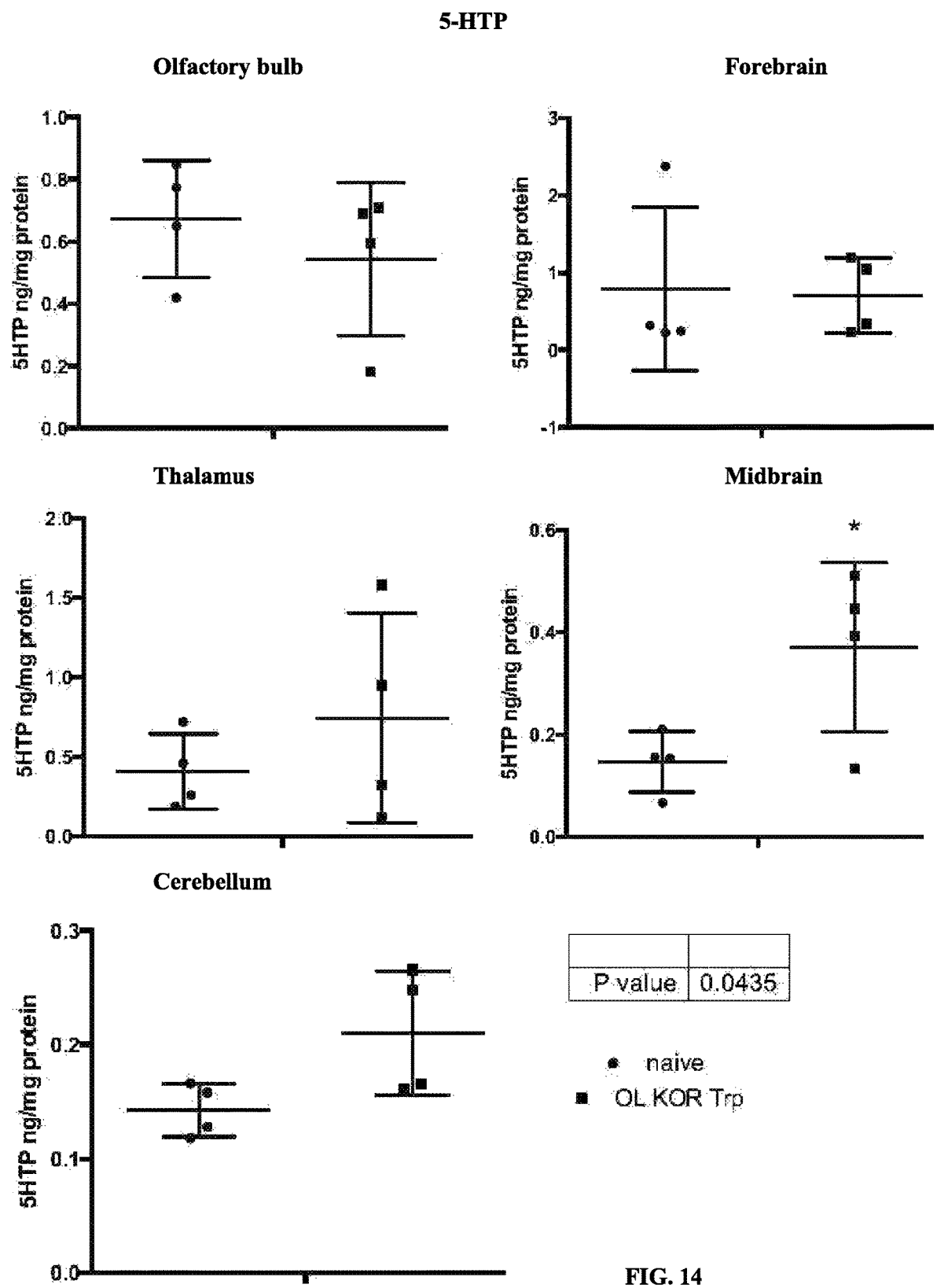
FIG. 14 is a series of plots showing results demonstrating that following intranasal administration of OLKOR-L1-5HTrp, 5-hydroxytryptophan accumulates predominantly in the mouse midbrain 30 minutes after intranasal administration.
Figure 16:
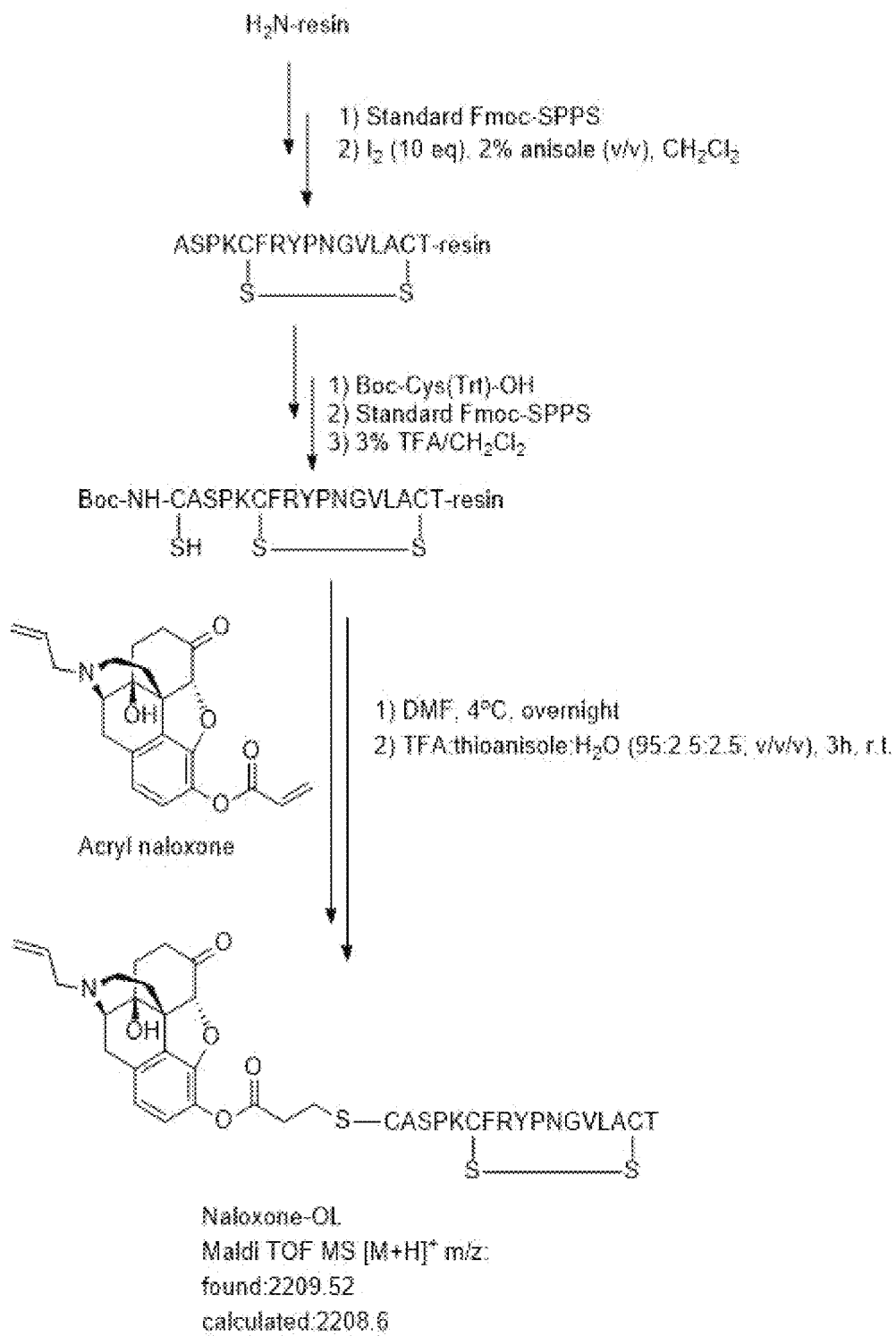
FIG. 16 is a schematic showing preparation of Naloxone-OL. The first amino acid sequence at the top of the figure is SEQ ID NO: 21, the second amino acid sequence (below the first amino acid sequence) is SEQ ID NO: 20, and the third amino acid sequence (below the second amino acid sequence) is SEQ ID NO: 17.

To demonstrate the feasibility of small molecule coupling to OL and to show that these conjugates exhibit biological activities, OLKOR-L1-5HTrp and OL-naloxone analogues were produced. 5HTrp, a serotonin biosynthetic precursors, was coupled to the N-terminal Ala of OL using standard solid-phase peptide synthetic protocol. 5HTrp was released from the OLKOR-L1-5HTrp scaffold as evidenced by the increased 5HTrp concentration in the mouse midbrain following intranasal administration of OLKOR-L1-5HTrp, FIG. 14. Naloxone is coupled to the OL scaffold using thiol-ene reaction. Naloxone is a μ-opioid receptor antagonist and reversal agent used to mitigate risk for opioid-induced respiratory depression by displacing the full opioid agonists. For this purpose, the N-terminal $Tyr^1$ in the OL sequence (SEQ ID NO: 1) was replaced with $Cys^1$, whereas acryl naloxone derivate required for thiol-ene reaction was prepared as described previously (Diego et al. Bioconjugate Chem. 2008, 19, 1767-1774). As Shown in FIG. 16, naloxone-OL was prepared by adding acryl naloxone to the peptidyl-resin precursor possessing N-terminal Cys with free thiol group. The final product OL-naloxone was purified by RP-HPLC as in the case of OL and related analogs its Mw was confirmed by MALDI-TOF MS analysis.

Compositions for treating a neurological disease, disorder and disabling condition in an individual include a therapeutically effective amount of a cyclic peptide or cyclic peptide conjugate as described herein and a pharmaceutically acceptable carrier. In some embodiments, the composition further includes a second therapeutic agent. In an embodiment of a composition for treating addiction, for example, the additional (second) therapeutic agent may be a drug that targets opioid receptors, dopamine receptors, serotonin receptors, cannabinoid receptors etc, and that is different from the opioid receptor ligand of the cyclic peptide or cyclic peptide conjugate. In an embodiment of a composition for treating Alzheimer's disease, for example, the additional (second) therapeutic agent may be an Alzheimer's disease treatment that is different from the biologically active peptide or protein or therapeutic agent (for treating Alzheimer's disease) of the cyclic peptide or cyclic peptide conjugate. In such embodiments, the cyclic peptide or cyclic peptide conjugate and the additional (second) therapeutic agent may have a synergistic effect.

Typically, the cyclic peptides, cyclic peptide conjugates and compositions are delivered to appropriate target cells in the individual (e.g., human patient or subject). A target cell is any cell in the CNS. In one embodiment, target cells are neurons. In other embodiments, target cells are non-neuronal cells. Cells to be targeted can be a mix of neuronal and non-neuronal cells. The cyclic peptides, cyclic peptide conjugates and compositions described herein may be used to treat any type of neurological disease or disorder or disabling condition, including for example, schizophrenia, meningitis, migraine, Parkinson's, Alzheimer's disease, pain and addiction, or a combination thereof.

Cyclic Peptide Combinatorial Libraries and Methods of Use Thereof

Figure 7:
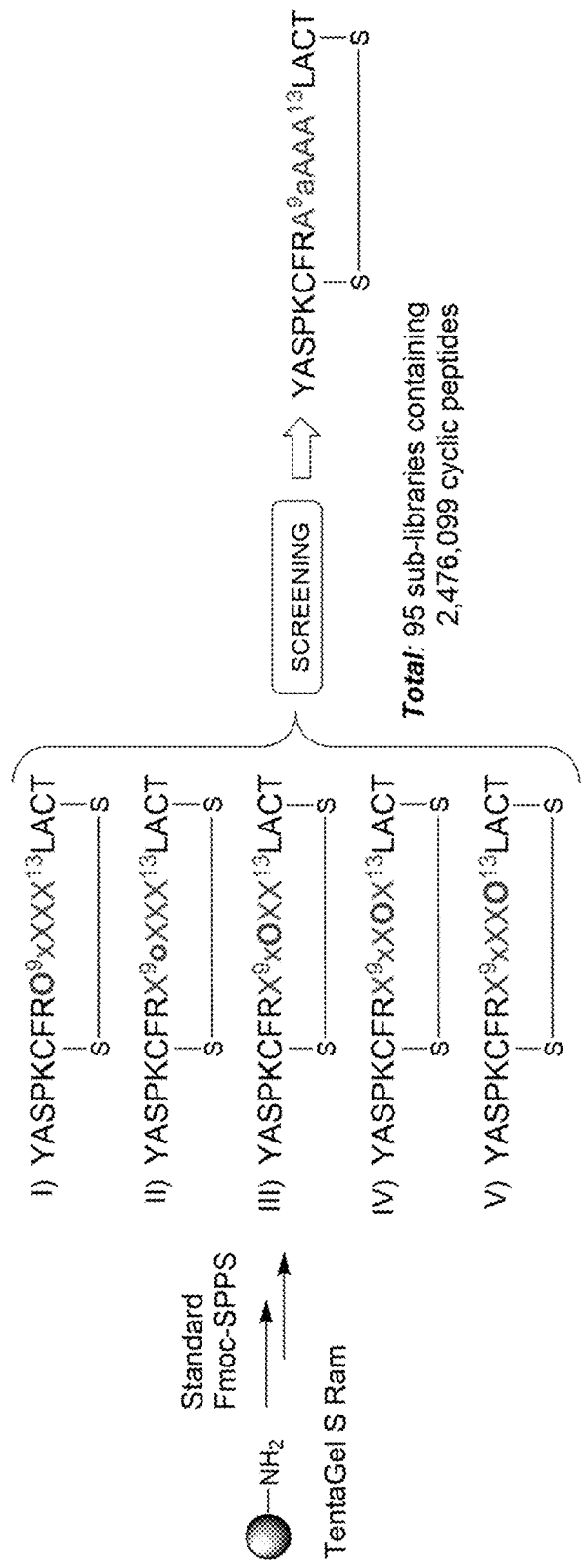
FIG. 7 shows sequences of the prepared positional scanning combinatorial library (PSCL). In these sequences, X represents a position composed of a mixture of 19 D- or L-amino acids; O represents a position defined with an individual amino acid; and A represents individual amino acids. According to IUPAC rules, lower case letters designate D-amino acids (e.g. D-alanine=a), whereas upper case letters designate proteinogenic L-amino acids (e.g. L-alanine=A). X (upper case) represents mixture of 19 L-amino acids. In these sequences, "x" (lower case) represents a mixture of 19 D-amino acids; "O" (upper case) represents a single L-amino acid; "o" (lower case) represents a single D-amino acid; and "a" (lower case) represents a D-amino acid.

Combinatorial libraries that include pluralities of cyclic peptides are described herein. The Examples below describe the generation of a positional-scanning synthetic combinatorial library containing 2,476,099 cyclic peptides (see FIG. 7). This library was made using modified Fmoc SPPS strategy (described in detail in Bionda et al., Eur J Med Chem 2016, 108, 354-363, Dooley, C T, Houghten, R, Life Sciences, 1993, 52: 1509-1517). A combinatorial library of cyclic peptides as described herein can be made using any suitable techniques. Such techniques are well-known in the art. Combinatorial library methods in drug discovery are known and are described, for example, in English, L. B. (2002) Combinatorial library methods and protocols, v. 201, Humana Press, Totowa, N.J.; and Agrafiotis, D. K. et al., (2002) Nature Reviews Drug Discovery 1:337-346. Combinatorial libraries such as positional scanning combinatorial libraries are described, for example, in Bionda et al., Eur J Med Chem 2016, 108:354-363; Ruiwu Liu et al., Curr Opin Chem Biol. 2017, 38:117-126; and Humet et al., J. Comb. Chem. 2003, 5:597-605; and U.S. patent application Ser. No. 15/145,901. All of these references are incorporated herein by reference.

In one embodiment, a combinatorial library includes a plurality of cyclic peptides of the general Formula I: $(X)_m$-Lys-cyclo-[Cys-Phe-$X_1$-$X_2$-$X_3$-Cys]-Thr (SEQ ID NO: 6). In this formula, X is an amino acid sequence having a length of m amino acids (m is at least 3); $X_1$ is a basic amino acid; $X_2$ is an amino acid sequence having a length of 5 amino acids; $X_3$ is an amino acid sequence having a length of 2 amino acids; and at least one of $(X)_m$ and $X_2$ includes a biologically active peptide or protein (e.g., an opioid receptor ligand or analogue thereof). A cyclic peptide may be a pharmaceutically acceptable salt thereof. In a cyclic peptide of Formula 1, X can be any protein or peptide sequence having a length (i.e., m) of at least 3 (e.g., 3, 4, 5, 6, 7, 8, 9, 10, etc.) amino acids, but can be up to several thousand amino acids in length. For example, X can be Tyr-Ala-Ser-Pro (SEQ ID NO: 4) which are amino acids 1-4 of the naturally occurring OL sequence (SEQ ID NO:1). The amino acids of X can be L-amino acids (e.g., all L-amino acids), D-amino acids (e.g., all D-amino acids), nonproteinogenic amino acids, proteinogenic amino acids, peptidomimetics, or a mix thereof. These amino acids can be naturally occurring amino acids, non-naturally occurring (synthetic) amino acids, or a mix thereof. Generally, the order and types of amino acids is determined based upon the interaction of the cyclic peptide with its biological target(s). In a cyclic peptide of Formula 1, $X_1$ can be any basic amino acid (e.g., Lys, Arg). This amino acid can be a naturally occurring amino acid or a non-naturally occurring (synthetic) amino acid. $X_1$ corresponds to position (amino acid) 8 of the naturally occurring OL sequence (SEQ ID NO: 1). In a cyclic peptide of Formula 1, $X_2$ can be any 5 amino acids, and corresponds to amino acids 9-13 of the naturally occurring OL sequence (SEQ ID NO: 1). These amino acids can be naturally occurring amino acids, non-naturally occurring (synthetic) amino acids, or a mix thereof. In a cyclic peptide of Formula 1, the amino acids of $X_3$ correspond to amino acids 14 and 15 of the naturally occurring OL sequence (SEQ ID NO: 1), and can be naturally occurring amino acids, non-naturally occurring (synthetic) amino acids, L-amino acids, D-amino acids, or a mix thereof. In a combinatorial library, a combinatorial modification can be done at the N-terminal part of the OL molecule, at the β-turn region, or both.

In another embodiment, a combinatorial library includes a plurality of cyclic peptides of the general Formula II: Tyr-Ala-Ser-Pro-Lys-cyclo [Cys-Phe-Arg-X-Leu-Ala-Cys]-Thr (SEQ ID NO: 18), or a pharmaceutically acceptable salt thereof. In this formula, X is an amino acid sequence having a length of 5 amino acids and is a mixture of D-amino acids and L-amino acids. These amino acids can be naturally occurring amino acids, non-naturally occurring (synthetic) amino acids, or a mix thereof. In one example of such a combinatorial library, at least a portion of the cyclic peptides have an affinity for at least one opioid receptor and the ability to modulate activity of the at least one opioid receptor (e.g., MOR, KOR and DOR). However, a combinatorial library as described herein can include cyclic peptides that have an affinity for any receptor of interest.

The combinatorial libraries can be used to identify a ligand for a receptor of interest, for example, to identify opioid cyclic peptides that have affinity for an opioid receptor. In one embodiment, a method of identifying at least one opioid cyclic peptide includes screening a combinatorial library as described herein using a suitable assay. Examples of such screening assays include competitive assays such as competition binding assays, competitive inhibition assays, and functional activity assays (e.g. cAMP and β-arrestin assays). Any suitable assays can be used. Additional examples include ex vivo bioassays for screening (e.g., the isolated guinea pig ilieum assay), and screening by administration to suitable animal species (e.g., rodents) and examining relevant physiological or behavioral effects (for opioids, these would include assays of respiration or analgesia, respectively). Once a candidate opioid cyclic peptide, for example, is identified, any suitable assay for testing opioid cyclic peptides for affinity, selectivity and activity can be used. For example, a variety of assays may be employed to test whether the cyclic peptides identified in a combinatorial library as described herein exhibit high affinity and selectivity for an opioid receptor. Receptor assays are well known in the art and μ-opioid receptor (MOR), δ-opioid receptor (DOR), and κ-opioid receptor (KOR) opioid receptors from several species have been cloned. Although these cloned receptors readily allow a particular candidate opioid cyclic peptide to be screened, natural sources of mammalian opioid receptors are also useful for screening, as is well known in the art (Dooley C T et al. J. Biol. Chem. 273:18848-56, 1998). Thus, screening against one or more of MOR, DOR and KOR, whether of recombinant or natural origin, may be carried out in order to determine the selectivity of candidate opioid cyclic peptides for the MOR, DOR or KOR. Additionally, candidate opioid cyclic peptides can be screened by administration to suitable animal species (e.g., rodents) and examining relevant physiological or behavioral effects such as respiration and analgesia.

Methods of Treating Neurological Diseases, Disorders, and Disabling Conditions in an Individual in Need Thereof Methods of treating neurological diseases, disorders and disabling conditions in an individual in need thereof include administering to the individual a pharmaceutically effective amount of a cyclic peptide or cyclic peptide conjugate as described herein, or a composition including the cyclic peptide or cyclic peptide conjugate, for treating (e.g., alleviating, ameliorating, curing) the neurological disease, disorder or disabling condition in the individual, and a pharmaceutically acceptable carrier. The methods include administration of any of the cyclic peptides, cyclic peptide conjugates and compositions described herein for treatment of any neurological disease, disorder or disabling condition (e.g., schizophrenia, meningitis, migraine, Parkinson's, Alzheimer's disease, pain, overdose and addiction, etc.). In a typical embodiment, a method of treating a neurological disorder in an individual includes administering to the individual a composition including a cyclic peptide or cyclic peptide conjugate as described herein via intranasal (i.n.) delivery to the individual's brain. In the methods, the cyclic peptides, cyclic peptide conjugates and compositions are capable of specifically binding to olfactory epithelial cells of the nasal mucosa and passaging across the mucosal barrier into the brain of the individual. In some embodiments in which the cyclic peptide includes or is conjugated to an opioid receptor ligand, administration of such a cyclic peptide modulates (e.g., activates or blocks) opioid receptor activity with low toxicity and low immunogenicity, e.g., without affecting normal cell viability in the individual (i.e., viability of the individual's normal (non-diseased) cells).

Cyclic peptides, cyclic peptide conjugates and compositions for treating neurological diseases, disorders and disabling conditions as described herein can be administered as a monotherapy or as part of a combination therapy with any other therapeutic agent in a method of treating a neurological disease, disorder or disabling condition in an individual in need thereof. In some embodiments of a combination therapy, a first composition may include a cyclic peptide or cyclic peptide conjugate as described herein, and a second composition may include another therapeutic agent. In such embodiments, the first composition may be administered at the same time point or approximately the same time point as the second composition. Alternatively, the first and second compositions may be administered at different time points.

Any suitable methods of administering a cyclic peptide, cyclic peptide conjugate or composition as described herein to an individual may be used. In these methods, the cyclic peptide, cyclic peptide conjugate or composition is administered to an individual intranasally. Methods of preparing a therapeutic agent in a form suitable for i.n. administration are well known in the art and are described, for example, in Bitter et al., Curr Probl Dermatol 2011, 40, 20-35; Pardeshi C. V. and Belgamwar V. S., Expert Opin Drug Deliv 2013, 10(8), 957-972; and Frey W. H., Drug Deliv. Techn. 2002, 2, 46-49, all incorporated herein by reference. The cyclic peptides, cyclic peptide conjugates, and compositions described herein may be administered i.n. to an individual (e.g., rodents, humans, nonhuman primates, canines, felines, ovines, bovines) in any suitable formulation according to the methods described in Bitter et al., supra, Pardeshi C. V. and Belgamwar V. S., supra, and Frey W. H., supra, and according to any conventional pharmaceutical practice (see, e.g., Remington: The Science and Practice of Pharmacy (21st ed.), ed. A. R. Gennaro, Lippincott Williams & Wilkins, (2005) and Encyclopedia of Pharmaceutical Technology, ($3^{rd}$ ed.) eds. J. Swarbrick and J. C. Boylan, Marcel Dekker, CRC Press, New York (2006), a standard text in this field, and in USP/NF). To prepare such a formulation, a therapeutically effective amount of a cyclic peptide or cyclic peptide conjugate as described herein is dissolved or suspended in a pharmaceutical carrier or vehicle. A description of exemplary pharmaceutically acceptable carriers and diluents, as well as pharmaceutical formulations, can be found in Remington: supra. Other substances may be added to the cyclic peptides, cyclic peptide conjugates and compositions to stabilize and/or preserve them.

The therapeutic methods described herein in general include administration of a therapeutically effective amount of the cyclic peptides, cyclic peptide conjugates, and compositions described herein to an individual (e.g., human) in need thereof, particularly a human. Such treatment will be suitably administered to individuals, particularly humans, suffering from, having, susceptible to, or at risk for a neurological disease, neurological disorder, disabling neurological condition or symptom thereof. Determination of those individuals "at risk" can be made by any objective or subjective determination by a diagnostic test or opinion of a subject or health care provider.

Effective Doses

The cyclic peptides, cyclic peptide conjugates, and compositions described herein are preferably administered to an individual in need thereof (e.g., human having one or more neurological diseases, disorders and disabling conditions) in an effective amount, that is, an amount capable of producing a desirable result in a treated individual. In the case of addiction, desirable results include one or more of, for example, prevention of drug reinforcing event, such as morphine conditioned place preference, and prevention of drug-induced reinstatement of extinguished drug-seeking behavior. In the case of schizophrenia, desirable results include for example, amelioration of positive affects (such as hallucinations) or negative effects (such as reversal of catatonia). In the case of meningitis, desirable results include for example, elimination of bacterial infection. In the case of migraine, desirable results include for example, amelioration or elimination of migraine-related pain. In the case of Parkinson's disease, desirable results include for example, restoration of normal locomotor activity and cognitive performance. In the case of Alzheimer's disease, desirable results include for example, restoration of cognitive performance. A therapeutically effective amount for a particular neurological disease, disorder, or disabling condition can be determined according to standard methods. Toxicity and therapeutic efficacy of the cyclic peptides, cyclic peptide conjugates, and compositions utilized in the methods described herein can be determined by standard pharmaceutical procedures. As is well known in the medical and veterinary arts, dosage for any one individual depends on many factors, including the individual's size, body surface area, age, the particular composition to be administered, time and route of administration, general health, and other drugs being administered concurrently. A delivery dose of a cyclic peptide, cyclic peptide conjugate or composition as described herein is determined based on preclinical efficacy and safety.

Kits

Described herein are kits for treating one or more neurological diseases, disorders, or disabling conditions in a subject. A typical kit includes a composition including a pharmaceutically acceptable carrier (e.g., a physiological buffer) and a therapeutically effective amount of a cyclic peptide or cyclic peptide conjugate as described herein; and instructions for use. A kit for treating a neurological disease, disorder, or disabling condition can also include a second therapeutic agent. Kits also typically include a container and packaging. Instructional materials for preparation and use of the compositions described herein are generally included. While the instructional materials typically include written or printed materials, they are not limited to such. Any medium capable of storing such instructions and communicating them to an end user is encompassed by the kits herein. Such media include, but are not limited to electronic storage media. Such media may include addresses to internet sites that provide such instructional materials.

EXAMPLES

The present invention is further illustrated by the following specific examples. The examples are provided for illustration only and should not be construed as limiting the scope of the invention in any way.

Example 1—Novel Cyclic Peptide-Based Platform for Intranasal Drug Delivery to the Brain Diseases of the CNS such as schizophrenia, meningitis, migraine, Parkinson's and Alzheimer's disease, along with other neurological disorders such as addiction, require delivery of the drug to the brain for effective treatment. However, conventional drug delivery methods are inefficient in delivering a number of therapeutic agents to the brain, especially hydrophilic and large molecular weight (MW) drugs such as peptides and proteins. Both the BBB and BCB restrict the transport of these therapeutic agents from systemic circulation into the CNS. The data described below demonstrate the utility of the cyclic peptide-based platform for i.n. drug delivery to the brain, including novel CNS peptide-based drugs suitable for i.n. delivery that have high selectivity, in vivo efficacy and tolerance. This approach to deliver peptide-based drug directly to the brain via the i.n. route has a variety of therapeutic and prophylactic applications, including, as non-limiting examples: analgesics, anti-convulsants, antidotes, addiction, anti-viral, antibiotics, anti-cancer, anti-inflammatory, and anti-neurodegenerative.

Individual Peptide Synthesis

The OL natural product (Li et al., PLoS One 2008, 3 (6), e2381), its analogues, and a control cyclic peptide composed of a randomly permutated OL sequence were synthesized, using a standard Fmoc-solid phase approach and on-resin disulfide bond formation by $I_2$ oxidation, Table 1. All peptides were purified by RP-HPLC and characterized by MALDI-TOF MS and analytical RP-HPLC.

TABLE 1

Receptor binding affinities ($K_d$/Nm) of OL and related peptides.

| | Asialofetuin* | Opioid receptors** | | |
| --- | --- | --- | --- | --- |
| | | δ | μ | K |
| OL | $6.4 \times 10^4$ | n.o. | n.o. | n.o. |
| DADLE | | 8 ± 3 (2.3) | 9 ± 2 (11.4) | 58 ± 22 |
| DADLE-OL | $4.2 \times 10^4$ | 64 ± 26 | 3538 ± 945 | $>10^4$ |
| DADLE-OL II | $3.3 \times 10^4$ | 275 ± 23 | 123 ± 41 | 1082 ± 139 |
| Control | $7.6 \times 10^5$ | $>10^4$ | $>10^4$ | $>10^4$ | n.o.: no binding observed under applied experimental conditions.
Control: RVFSL-cyclo[CNATYPYKGAC]P (SEQ ID NO: 19)
*$K_d$ values for asialofetuin were determined by ITC.
**$K_d$ values were determined in a protein binding radioassay.
DADLE-OL: bioactive sequence grafted in the β-turn region.
DADLE-OL II: YaGFIK-cyclo[CFRYPNGVLAC]T (SEQ ID NO: 9); bioactive sequence grafted in the N-terminal region.
Parenthesis: literature data (Janecka et al. Acta Paediatr Suppl 2003, 92 (443), 83-91)

Binding Studies

Grafting the DADLE fragment into the OL scaffold resulted in a novel cyclic opioid-like peptide (DADLE-OL) retaining the functional properties of the parent peptides, FIG. 2. DADLE-OL exhibits almost identical affinity toward L-fucose bearing asialofetuin (model glycoprotein) as the unmodified OL, Table 1. In addition, DADLE-OL binds DOR with an affinity approximately one order of magnitude lower than DADLE, but improved selectivity for DOR over MOR, Table 1. The lack of a positively charged N-terminal Tyr residue and the conformational constraint may explain lower affinity of DADLE-OL toward DOR in comparison to DADLE. The unmodified OL does not bind any of the three opioid receptors tested, Table 1. To confirm that the residues 5-7, 16 and 17 in the OL scaffold are crucial for fucose binding, a control peptide composed of a scrambled OL sequence was synthesized, Table 1. As expected, affinity of the control peptide toward asialofetuin is significantly lower compared to OL, indicating that these residues are not amenable to modification. Similar affinity toward asialofetuin was observed for DADLE-OL II. However, this peptide exhibits lower affinity toward DOR and does not discriminate between MOR and DOR.

In Vivo Activity

Figures 3A, 3B:
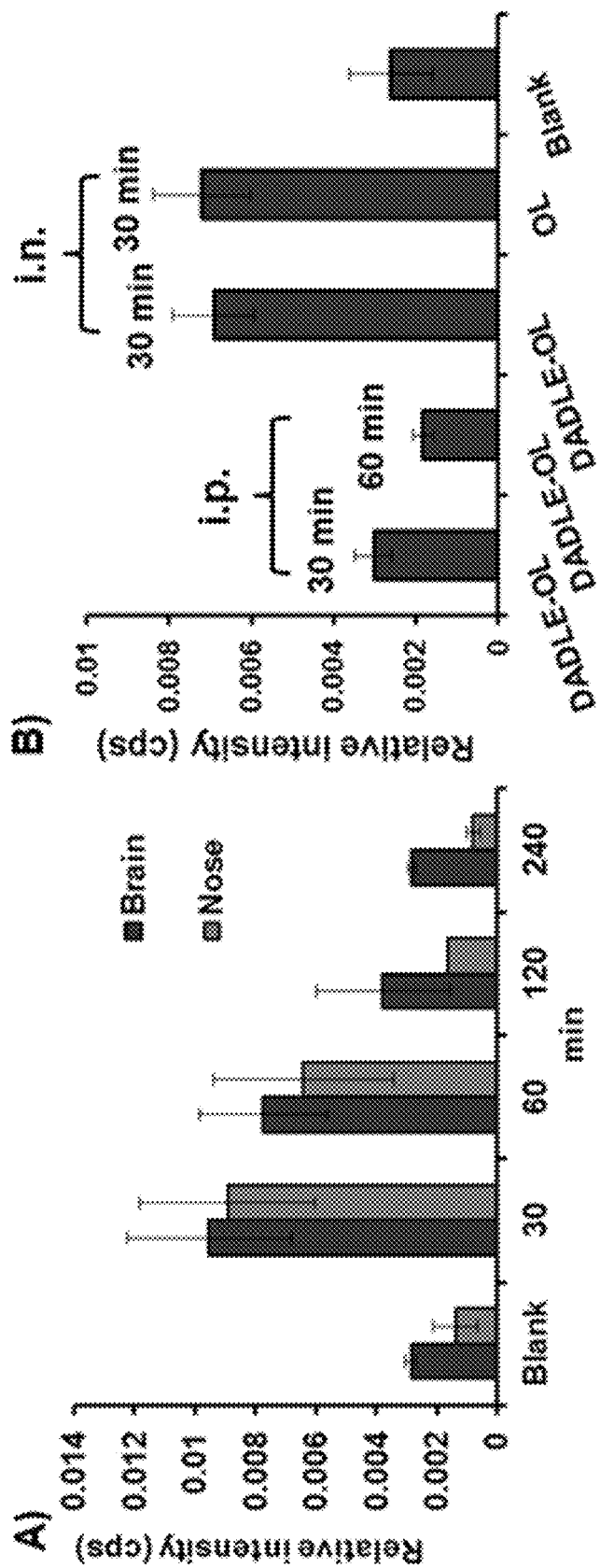
FIG. 3A is a graph showing accumulation of OL in the mouse brain and nose after i.n. administration (30 μg, 6 μL/nostril).
FIG. 3B is a graph showing accumulation of DADLE-OL and OL in the mouse brain after intraperitoneal (i.p.) (2 mg/mL, 250 μL/25 g mouse) and i.n. (30 μg, 6 μL/nostril) administration. Peptide level in the brain was determined by LC-MS/MS. All experiments were done in triplicate. Blank: tissue with added IS after samples were collected.
Figure 4:
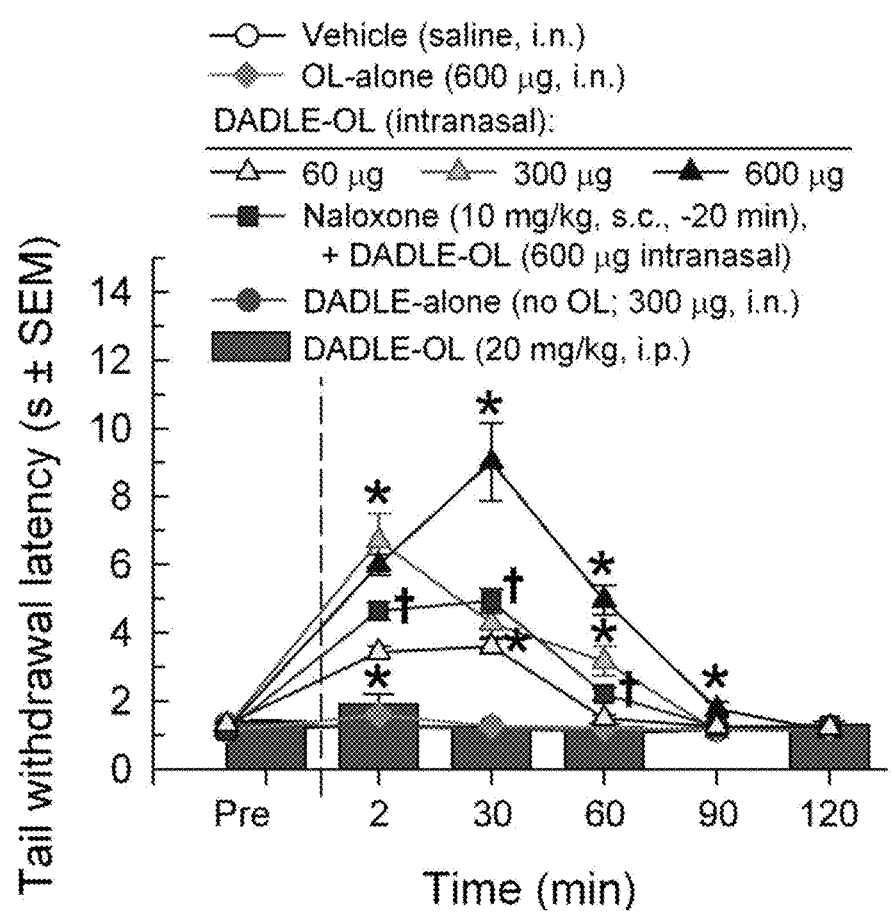
FIG. 4 is a graph showing antinociceptive effects of synthesized peptides after i.n. and i.p. administration. Points=8 mice. *=$p<0.05$ vs. pre-admin latency; †=$p<0.05$ vs. 600 μg DADLE-OL latency at same time.

OL and its analogue DADLE-OL can be detected in the mouse brain 30 minutes after i.n. administration, and it was eliminated from the brain in about 240 minutes, FIG. 3A. The level of OL in the mouse brain at the selected time intervals parallels those in the mouse nose. The level of DADLE-OL in the mouse brain 30 minutes after i.n. administration was identical to the level of OL, indicating that grafting of DADLE sequence into OL did not affect its nose-to-brain transfer ability, FIG. 3B. No DADLE-OL was detected in the mouse brain 30 and 60 minutes after i.p. administration. The functional activity of DADLE-OL was evaluated by antinociception produced in vivo in mice measured with the 55° C. warm water tail-withdrawal test, FIG. 4. Although no adverse effects were observed in mice at the highest tested i.n. doses of OL and DADLE-OL, only DADLE-OL exhibited dose- and time-dependent antinociception. Significant effects were observed at all tested doses 2 minutes after i.n. administration, with the peak effect 30 minutes after administration of 600 μg, FIG. 4. DADLE-OL failed to show significant antinociceptive activity after i.p. administration, and i.n. administration of the individual parent peptides, DADLE and OL, did not themselves produce antinociception. Furthermore, when DADLE-OL was administered to mice lacking MOR or KOR, or to mice pretreated with the opioid antagonist naloxone or DOR-selective antagonist naltrindole, the tail withdrawal test results show a decreased response only in mice lacking MOR and in mice pretreated with naloxone, suggesting that DADLE-OL-mediated antinociception was predominantly MOR-mediated. This is expected because DADLE-OL does not bind KOR, Table 1, and because of its mixed MOR/DOR activity, similar to the parent DADLE.

Figure 5:
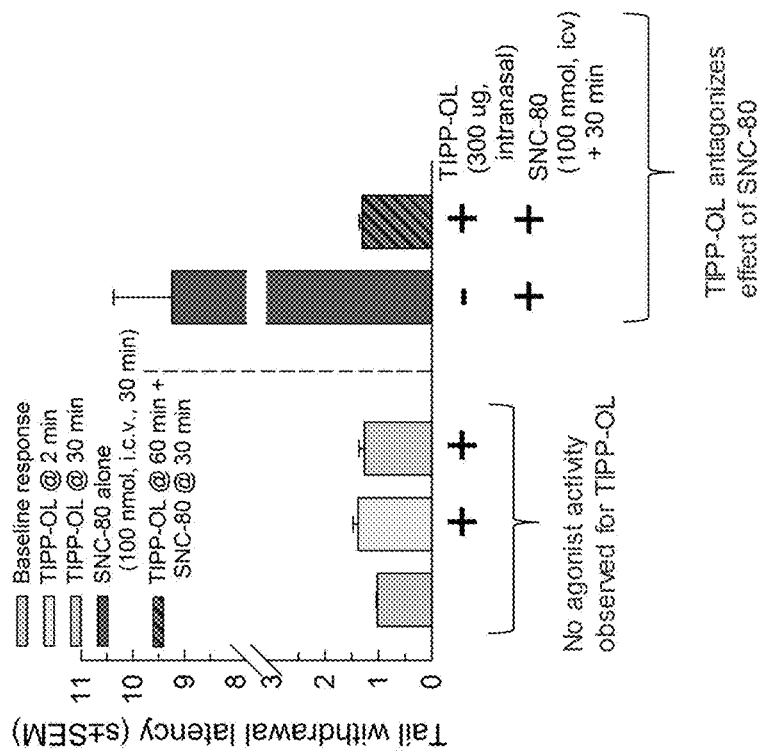
FIG. 5 is an amino acid structure and a graph showing that TIPP-OL fully reverses the effect of a potent DOR agonist SNC-80 in mice after i.n. administration. TIPP=Tyr-Tic-Phe-PheOH (SEQ ID NO: 2).
Figure 5:
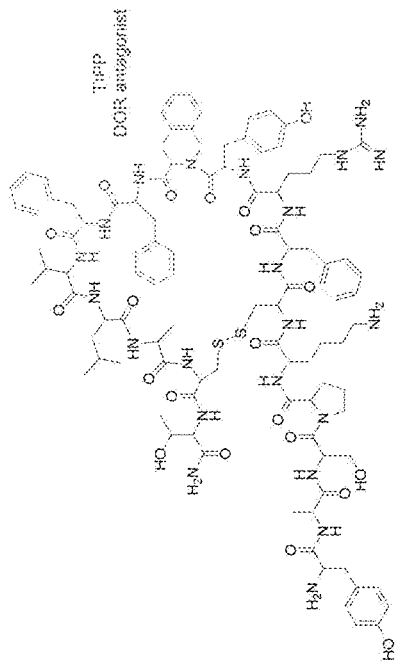

Although DADLE-OL induces significant antinociceptive effects in mice following i.n. administration, no impairment in motor coordination was observed using the rotarod test. In contrast, U50,488, a κ-opioid receptor agonist used as a positive control, significantly impaired motor coordination in mice following i.p. administration. To demonstrate that the ligands exhibiting different opioid activity can be delivered into the brain via the i.n. route, a TIPP-OL analogue was prepared, FIG. 5. This analogue was prepared by grafting (conjugating) a sequence of known DOR antagonist TIPP (Tyr-Tic-Phe-PheOH [SEQ ID NO: 2]) (Schiller et al. Biopolymers 1999, 51 (6), 411-25.), using the same synthetic approach as described previously. As shown in FIG. 5, TIPP-OL fully antagonizes the effect of a potent DOR agonist SNC-80 in mice. In this experiment SNC-80 was i.c.v. administered following pretreatment with i.n. administration of TIPP-OL.

Figure 6:
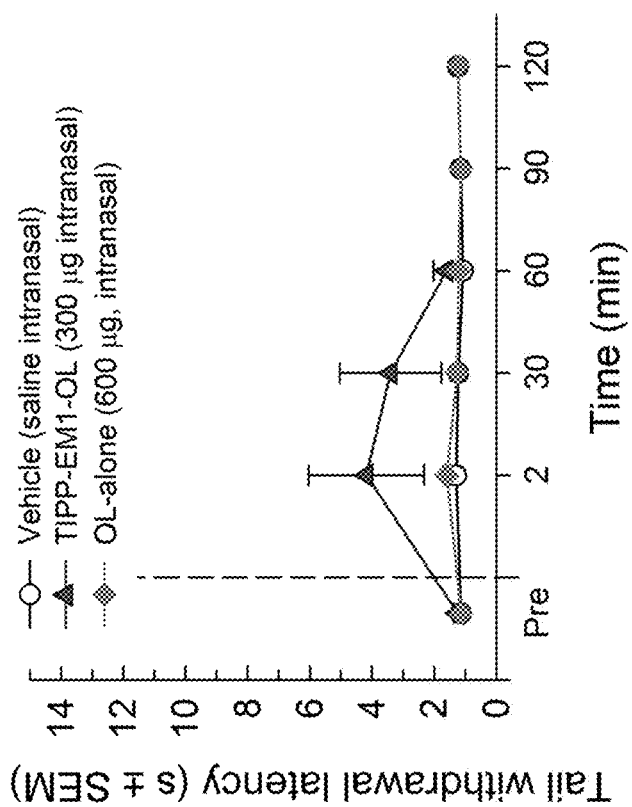
FIG. 6 is an amino acid structure and a graph showing the antinociceptive effects of bifunctional TIPP-EM1-OL. TIPP=Tyr-Tic-Phe-PheOH (SEQ ID NO: 2). Endomorphin 1=Tyr-Pro-Trp-Phe-NH$_2$ (SEQ ID NO: 3). Tic=1,2,3,4-tetrahydroisoquinoline-3-carboxylic acid.
Figure 6:
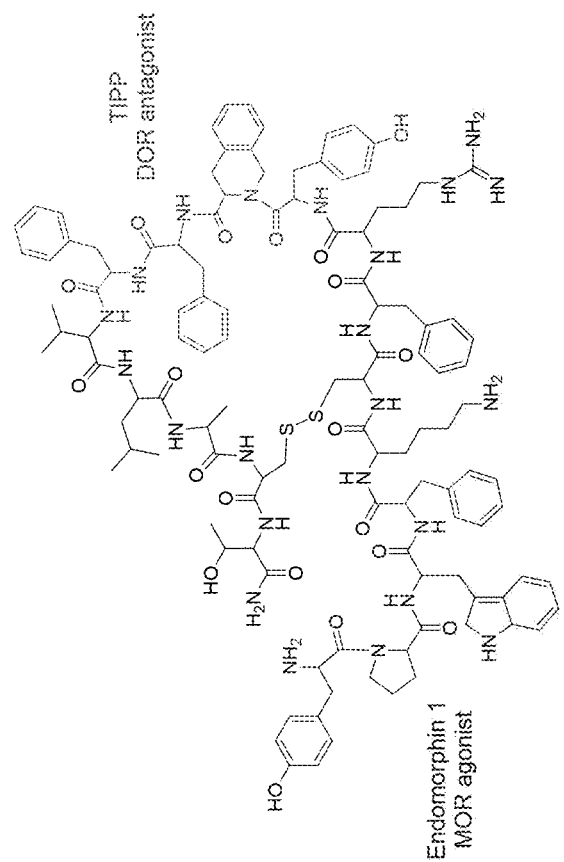

Based on the literature evidences showing that opioid compounds with mixed i agonist/δ antagonist properties may exhibit an antinociceptive effect with low propensity to induce side effects, bifunctional OL analogue, TIPP-EM1-OL, containing the i agonist endomorphin 1 (EM1) (Zadina et al., Nature. 1997; 386(6624):499-502, Tyr-Pro-Trp-Phe-$NH_2$ (SEQ ID NO: 3) grafted into the N-terminus and antagonist TIPP grafted into the β-turn region of the OL scaffold, was prepared, FIG. 6. Although not as potent as other OL analogues, TIPP-EM1-OL exhibits antinociceptive effects in mice following the i.n. administration. This experiment unequivocally demonstrated the suitability of the odorranalectin scaffold for a variety of chemical modifications (e.g., insertion of peptide sequences composed of L-, D- and nonproteinogenic amino acids; insertion of peptidomimetics; insertion of small molecules; insertion of proteins).

Optimization of OL-based Opioid Ligands

To validate this approach and to identify novel opioid ligands based on the OL scaffold, a focused PSCL of 2,476,099 cyclic peptides was produced, and this library was screened for affinity toward μ, δ and κ opioid receptors. The cyclic peptides in the prepared combinatorial library possess an unmodified fucose binding region (residues 5-7, 16 and 17 of SEQ ID NO: 1), whereas the sequence responsible for opioid receptors binding (residues 9-13 of SEQ ID NO: 1) was randomized.

Library Synthesis

The cyclic peptide synthetic combinatorial library was generated by the process of divide, couple and recombine using 19 commercially available D- and L-amino acids (Cys is omitted to avoid formation of more than one disulfide bond) using modified Fmoc SPPS strategy previously developed (Bionda et al., Eur J Med Chem 2016, 108, 354-363; Dooley, C T, Houghten, R, Life Sciences, 1993, 52: 1509-1517), FIG. 7. The comparison of several endogenous and synthetic opioid ligands showed that the opioid peptide sequence needs the presence of Pro or D-amino acid in position 2 for good interaction with opioid receptors. To maintain the same order of D- and L-amino acids as they appear in the sequences of these opioid ligands in the synthesized cyclic peptides, position 10 contains D-amino acids (corresponds to the position 2 in the sequences of endogenous and synthetic opioid ligands) whereas remaining positions in the OL sequence responsible for opioid activity were composed of L-amino acids. Using this approach, five sets of 95 cyclic peptide sub-libraries were prepared. The first set of 19 sub-libraries had specifically defined amino acids in position 9 of the sequence, and the remaining four positions consisted of mixtures of the 19 D- or 19 L-amino acids. The next set of cyclic peptide sub-libraries were defined by the amino acid in position 10, and the remaining positions contained all possible amino acid combinations. This process was thus repeated for the remaining amino acid residues. Variable positions were incorporated by coupling of a mixture of 19 Fmoc-protected amino acids in predetermined molar ratios to compensate for different coupling rates. However, protocol for on-resin disulfide bond formation using an oxidizing agent had to be optimized to avoid or minimize Met oxidation and Trp-peptide bond cleavage. For this purpose, use of N-chlorosuccinimide (NCS) was explored as an oxidizing agent for on-resin disulfide formation. Based on the literature reports, NCS is compatible with oxidation-prone Met and Trp, and it is compatible with peptides containing Boc and Trt protecting groups. It was found that 1.1 eq of NCS over a 1.5 hour period leads to complete disulfide bond formation with cca 60% Met oxidation. However, oxidized Met residues in peptide thioesters can be reduced rapidly with $NH_4I$ to the corresponding sulfide by using $(CH_3)_2S$ as co-reductant. Addition of 20 eq of $NH_4I$ and 20 eq of $(CH_3)_2S$ into the reaction mixture and shaking this mixture at room temperature for 2 hours resulted in complete reduction of oxidized Met without destruction of the existing disulfide bridge. Under the applied experimental conditions for on-resin disulfide bond formation, no cleavage of tryptophanyl peptide bond was observed. The completion of peptide coupling was monitored by the Kaiser (ninhidryn) test and the Ellman test was carried out to monitor the completion of disulfide bond formation. Using the described optimized synthetic strategy, a PSCL containing 2,476,099 cyclic peptides was generated, FIG. 7.

Library Screening for Binding to Opioid Receptors

The prepared PSCL was screened for the identification of novel cyclic opioid-like peptides in three different competitive assays using human opioid clones expressed in CHO cells. Competition binding assays were conducted using [$^3$H]-DAMGO, [$^3$H]-DSLET and [$^3$H]-U69,593 as MOR, DOR and KOR radioligands, respectively. In brief, binding assays were carried out in 1 mL polypropylene tubes in a 96-well format, and the reaction was terminated by filtration through GF-B filters. Bound radioactivity was counted on an LKB β-plate Liquid Scintillation Counter. Competitive inhibition assays were performed using 0.2 and 1 mg/mL of peptide mixtures. The assays were repeated twice. Screening assay showed significantly stronger affinities of synthesized peptides toward MOR than toward DOR and KOR. Use of 1 mg/mL of peptide mixtures in the screening assays clearly indicated amino acid residues responsible for selective DOR and KOR binding. On the other hand, 0.2 mg/mL of peptide mixtures showed significant inhibition (up to 60%) of radioligand binding only for MOR. Amino acid residues that drive opioid receptor selectivity are shown in Table 2. The performed screening assay provided valuable structure-binding data and clearly demonstrated the feasibility of this approach to identify individual OL-based cyclic peptides selective for MOR, DOR and KOR.

TABLE 2

Selected amino acid residues responsible for selective MOR, DOR and KOR binding. Cyclic peptide sequence: NH$_2$CO-T-*cyclo*[C-A-L-X$_5$-X$_6$-X$_7$-X$_8$-X$_9$-R-F-C]-K-P-S-A-Y-NH$_2$

| Position Receptor | X$_5$ | X$_6$ | X$_7$ | X$_8$ | X$_9$ |
|---|---|---|---|---|---|
| MOR | N | V | P | v | H |
|  | | H | T | p | M |
|  | | | P | | |
| DOR | G | S | V | l | A |
|  | D | E | T | d | D |
|  | | | P | p | |
|  | | | F | g | |
|  | | | | l | |
| KOR | R | K | R | m | R |
|  | P | W | A | l | P |
|  | A | | | v | |
|  | | | | f | |

Example 2—Additional Cyclic Compounds and Use Thereof

Modification of the N-terminal Part of OL

Figure 8:
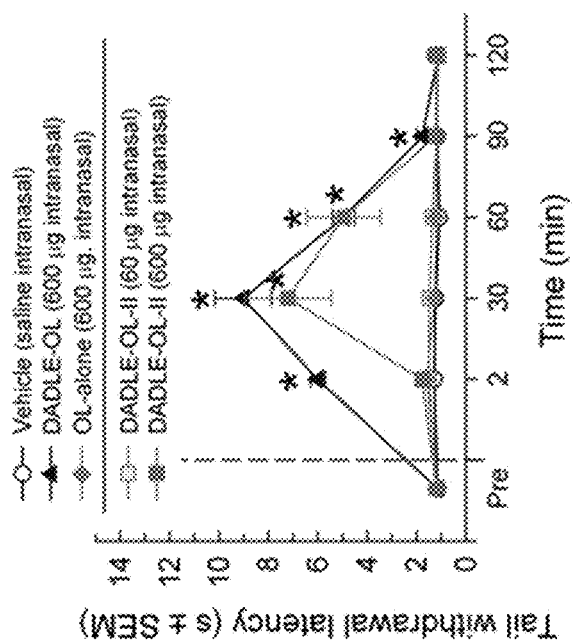
FIG. 8 is an amino acid structure and a graph showing the antinociceptive effects of a synthesized DADLE-OL II analogue.
Figure 8:
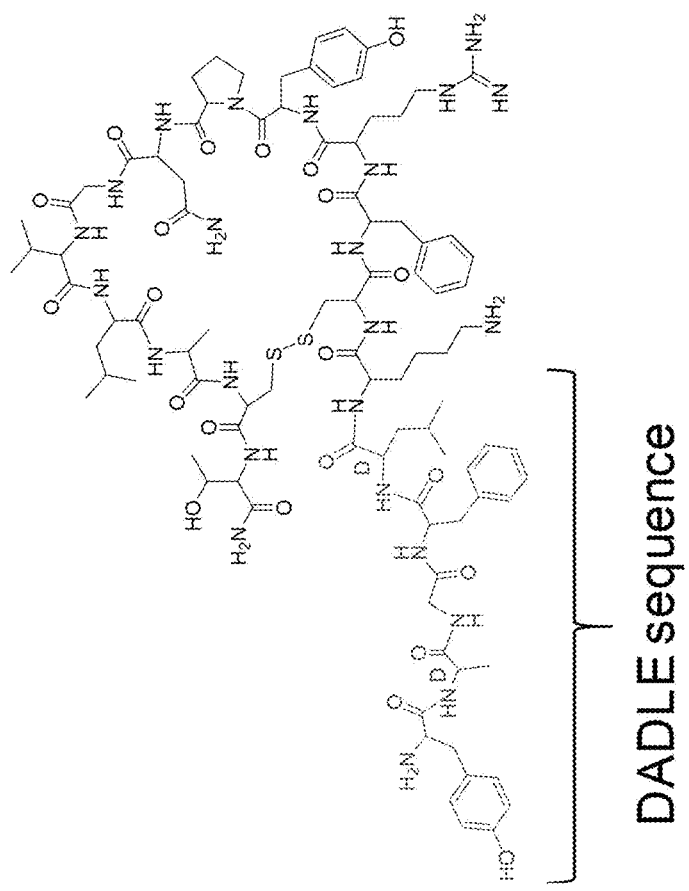
Figure 9A:
FIG. 9A is OLMOR-L1 amino acid sequence (SEQ ID NO: 12), a potent novel MOR agonist, OLMOR-L1, identified from screening of an OL-based combinatorial library.
Figure 9B:
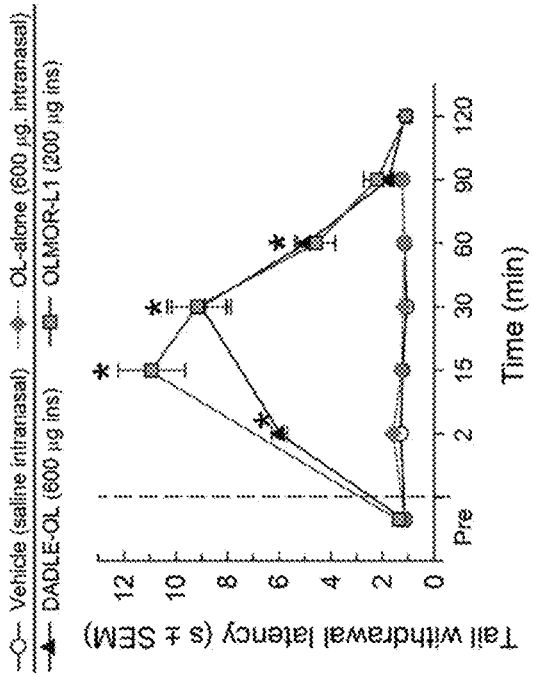
FIG. 9B is a graph showing rapid activity and dose response of OLMOR-L1 following i.n. administration.
Figure 9C:
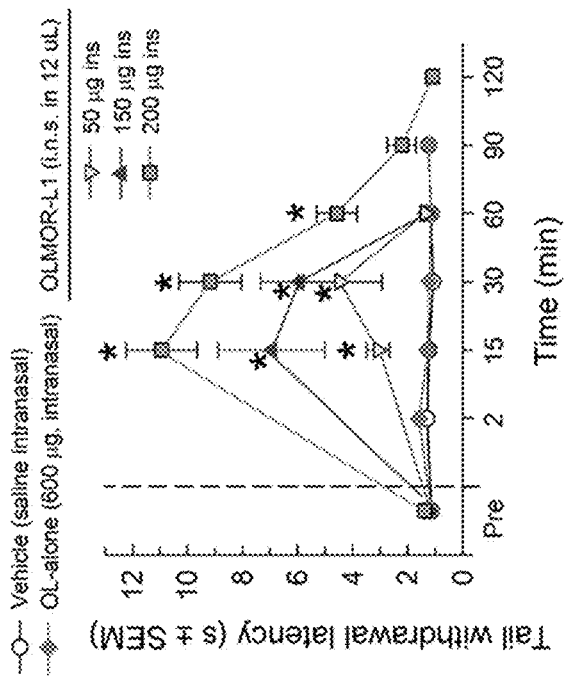
FIG. 9C is a graph showing improved potency of OLMOR-L1 in comparison to the parent DADLE-OL.
Figure 9D:
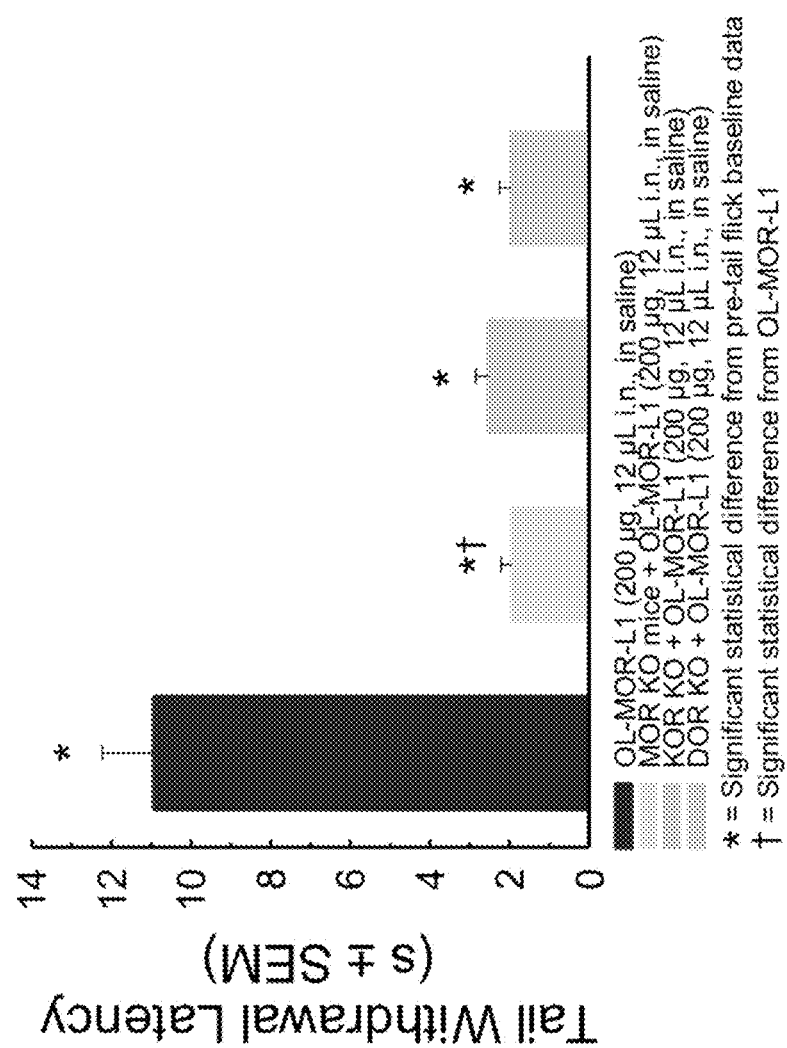
FIG. 9D is a graph showing antinociception in wild-type, MOR-KO, KOR-KO, and DOR-KO mice using tail-withdrawal test indicating lack of in vivo opioid receptor selectivity of OLMOR-L1.
Figure 10:
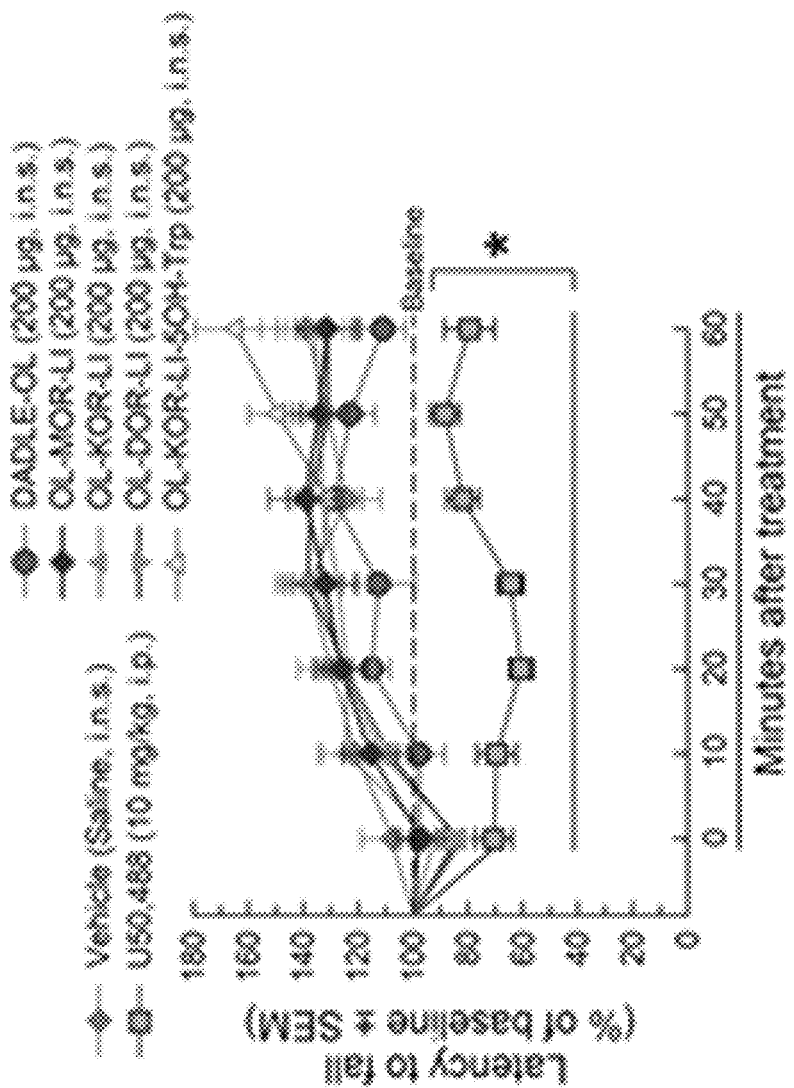
FIG. 10 is a graph showing the effects of OL-based opioid ligands on mice motor coordination and balance.

DADLE-OL II was prepared to assess the effect of modification of the N-terminal part of OL on the peptide's biological activity, FIG. 8. In the DADLE-OL II, OL's four N-terminal amino acids (Tyr$^1$-Ala$^2$-Ser$^3$-Pro$^4$) (SEQ ID NO: 4) were replaced with the DADLE sequence. As shown in Table 1, DADLE-OL II binds asialofetuin with an affinity (K$_d$=33 μM) similar to OL (K$_d$=42 μM), Table 1, suggesting that this modification does not affect the peptide's binding to carbohydrates and thus its ability to transit from nose to the brain. However, lower affinity (K$_d$=275 nM) was determined for DOR in comparison to DADLE-OL (K$_d$=64 nM) and this peptide does not discriminate between MOR and using the knockout mice, FIG. 9D. As shown in FIG. 10, OLMOR-L1 did not affect motor coordination and balance in mice using the rotarod test, suggesting a possibility for fewer side effects. In addition, this peptide did not induce significant conditioned place preference or aversion in mice. A lack of conditioned place preference observed for OLMOR-L1 could possibly be explained by this peptide's absence of in vivo selectivity toward opioid receptors. With synthesis and assessing the analgesic activity of OLMOR-L1 in a tail-withdrawal assay, it was demonstrated that it is possible to identify more potent OL-base opioid ligands using the described combinatorial chemistry approach.

Figure 11:
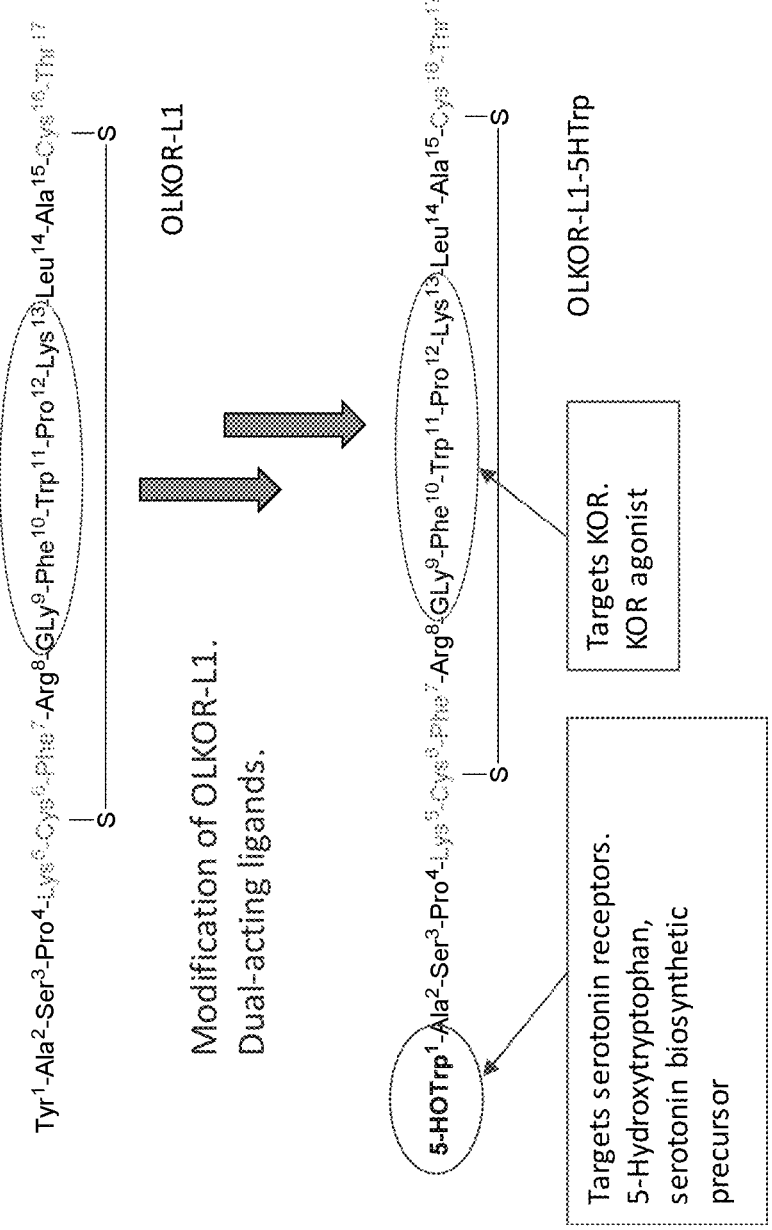
FIG. 11 shows amino acid sequences of novel dual-acting OL-based ligands as described herein. The top sequence is SEQ ID NO: 11, and the bottom sequence is SEQ ID NO: 13.
Figure 12:
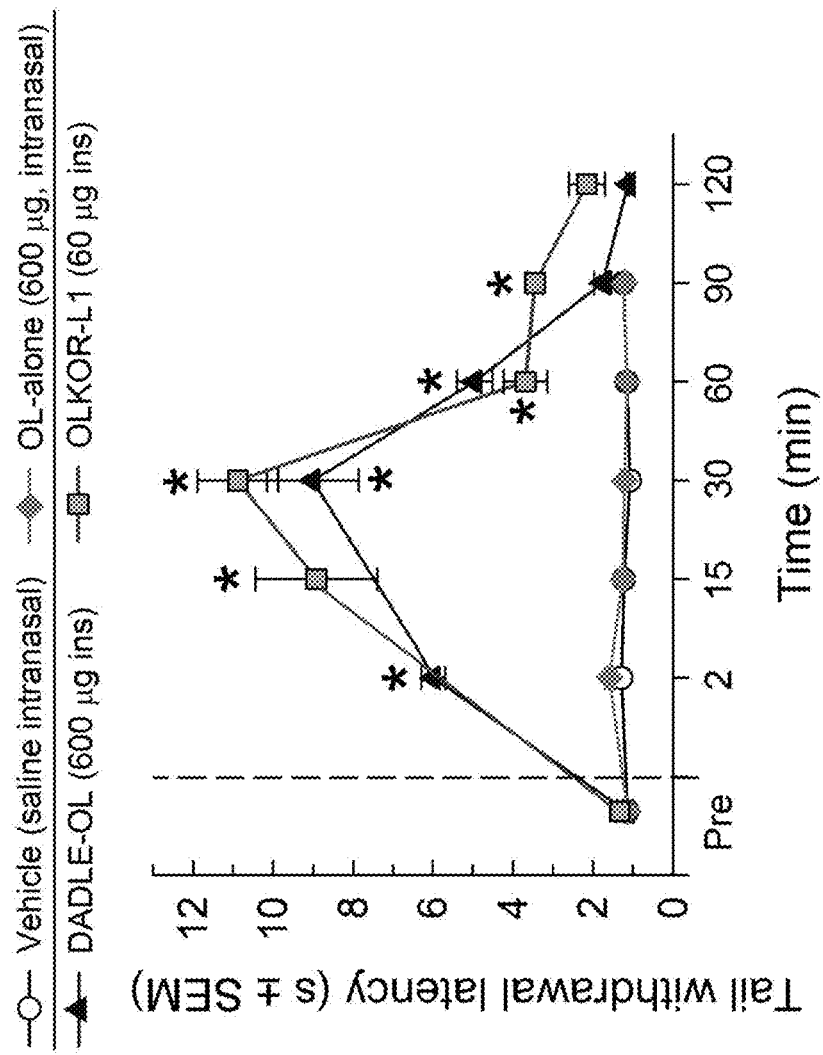
FIG. 12 is a graph showing antinociceptive activity of OLKOR-L1 in the mouse 55° C. warm water tail withdrawal assay following i.n. administration.
Figure 13A:
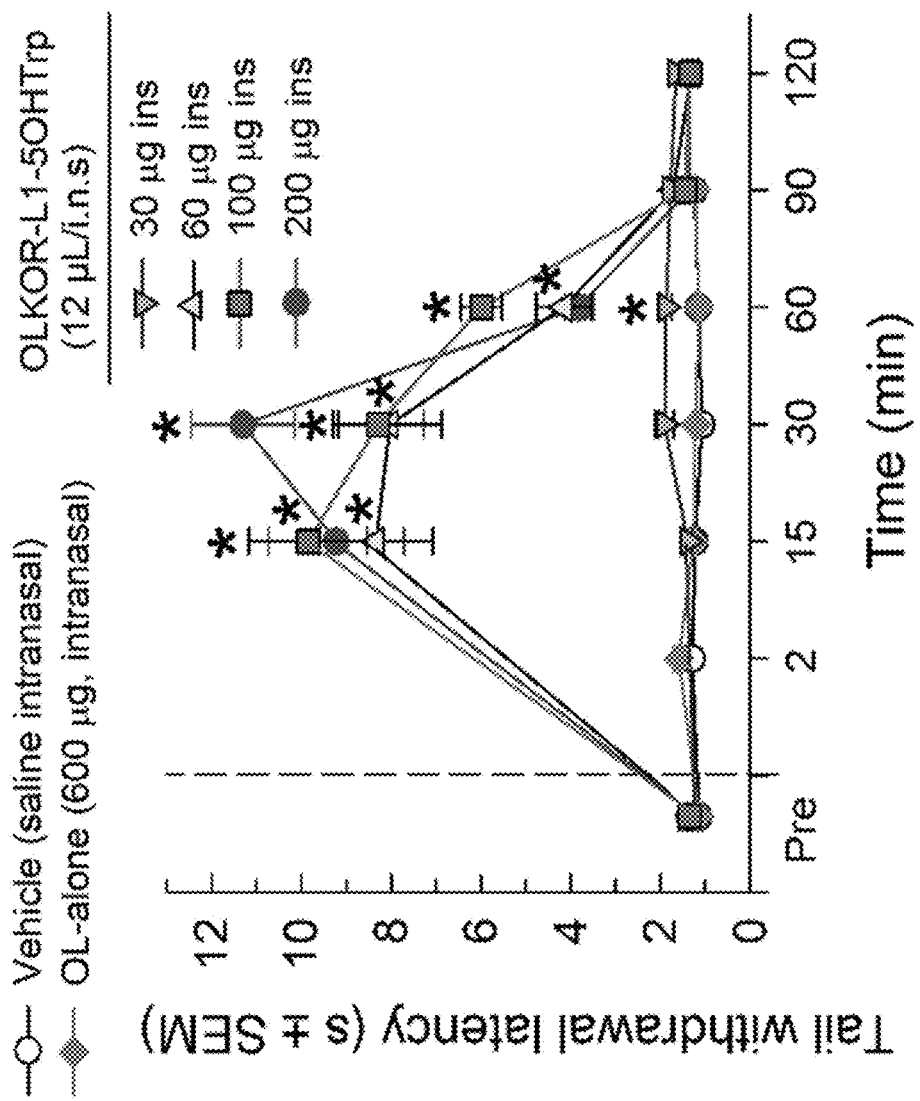
FIGS. 13A, 13B, and 13C are graphs showing in vivo activities of OL-based OLKOR-L1, OLKOR-L1-5HTrp, and OL-5HTrp.
Figure 13B:
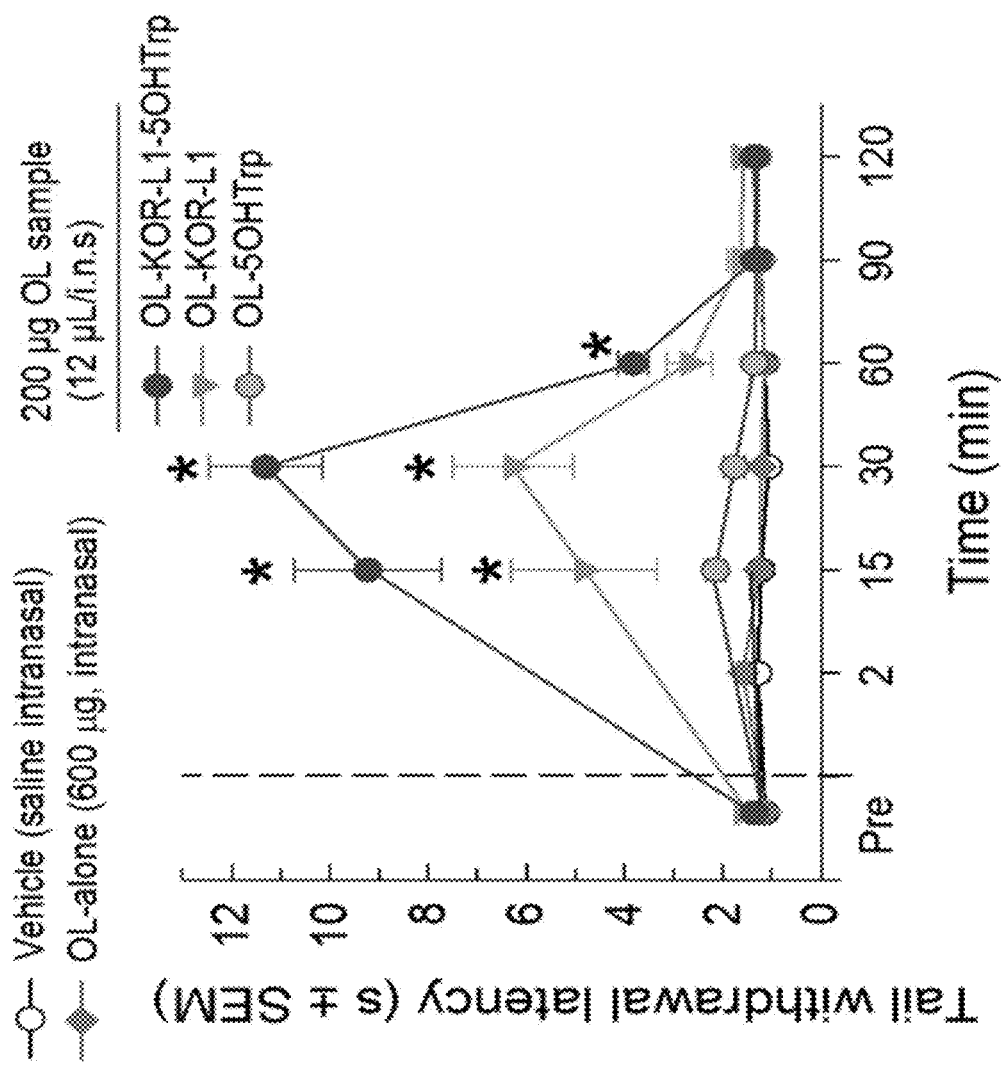
Figure 13C:
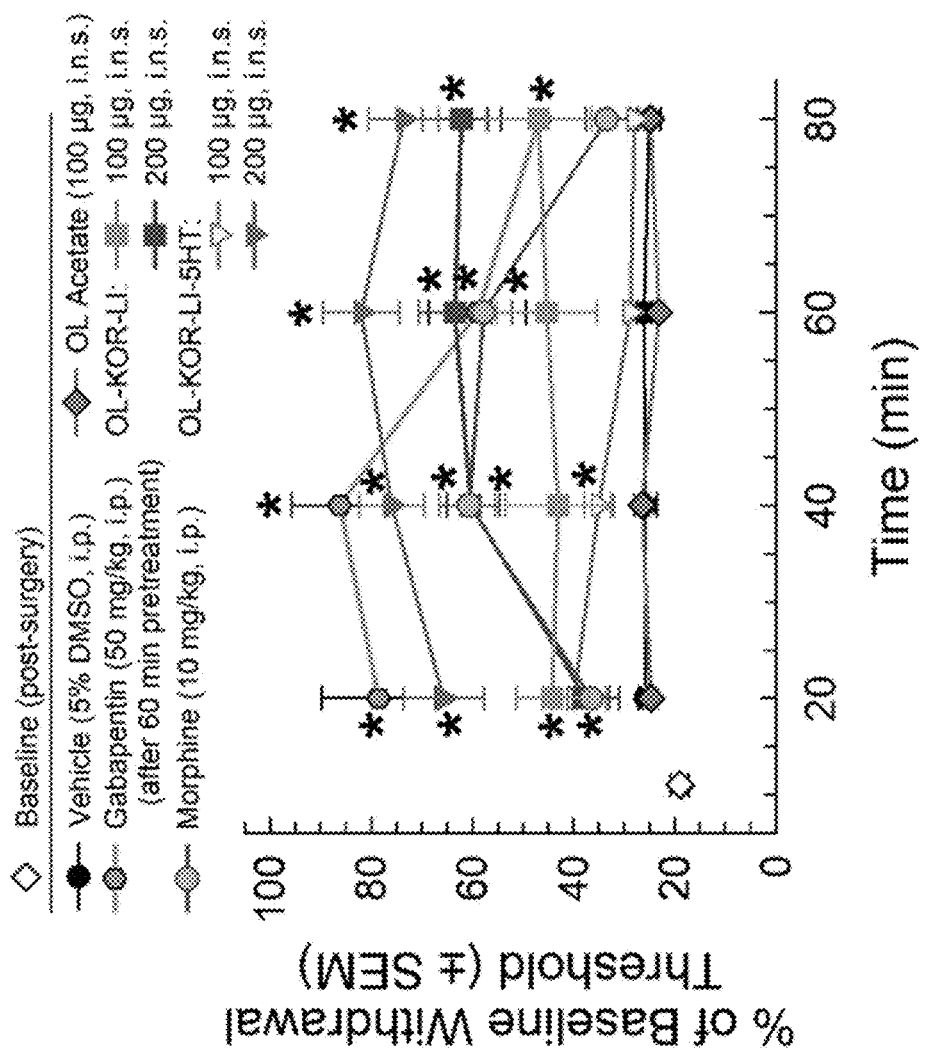

Similarly, a novel OL-based KOR ligand, OLKOR-L1, was identified based on the OL combinatorial library screening, FIG. 11 and Table 2. Marked improvement in analgesic activity was observed for OLKOR-L1, FIGS. 12 and 13C. OLKOR-L1 exhibited dose and time dependent antinociception in the mouse 55° C. warm water tail withdrawal assay following i.n. administration, with the peak activity observed after 30 minutes at a dose of 60 μg/mL. At 60 μg/mL OLKOR-L1 showed approximately 20% more potent antinociception in mice than the DADLE-OL at 600 μg/mL measured with the tail withdrawal test, FIG. 12. Importantly, OLKOR-L1 also exhibits antiallodynic effects in the mouse chronic constriction injury (CCI) model of neuropathic pain, FIG. 13C. In this experiment, the analgesic efficacy of OLKOR-L1 (200 μg, i.n.) was comparable to the effect of morphine (10 mg/kg, i.p.), but with reduced loss of activity over 80 minutes as was the case for morphine. Importantly, no impairment in motor coordination in mice was observed in the rotarod test, FIG. 10, and no other adverse effects were observed following the i.n. administration of OLKOR-L1 (100 μg), positioning OLKOR-L1 as a significant improvement over traditional opioid drugs. In addition, the conditioned place preference (CPP) data indicated that OLKOR-L1 does not produce reward (characteristic of morphine) nor conditioned place aversion (CPA)—characteristic of traditional dysphoria produced by KOR agonists) in mice.

Neurotransmitters serotonin and norepinephrine have been implicated as primary mediators of endogenous analgesic mechanisms in the pain pathway. Preclinical data suggests that persistent and neuropathic pain may be inhibited by enhancement of serotonin and norepinephrine transition, and deficiencies in one or both of these neurotransmitters may contribute to perception of pain. Moreover, animal studies have shown that SNRIs block pain-related behaviors. To test if the combination of KOR agonist activity with simultaneous delivery of norepinephrine and/or serotonin into the brain may improve OLKOR-L1 analgesic activity as well as neutralize the undesired side effects associated with KOR activation (polypharmacy approach), an OLKOR-L1 analogue was prepared. N-terminal $Tyr^1$ and $Ala^2$ in the OLKOR-L1 sequence that are rapidly hydrolyzed under physiologically relevant conditions are ideally suited for replacement with 5-hydroxy tryptophan (5-HTrp), L-3, 4-dihydroxyphenylalanine (L-DOPA), or their analogues and thus for the delivery of these molecules to the brain. OLKOR-L1 possessing N-terminal 5-HTrp (OLKOR-L1-5HTrp) was prepared, FIG. 11, and its in vivo activity was assessed, FIG. 13. OLKOR-L1-5HTrp exhibited dose and time dependent antinociception in the mouse 55° C. warm water tail withdrawal assay following i.n. administration, with the peak activity observed after 30 minutes at a dose of 60 μg/mL, FIG. 13A. In comparison to the parent OLKOR-L1 and the controls, morphine and gabapentin, OLKOR-L1-5HTrp (200 μg, i.n.) showed significant improvement in the analgesic efficacy in the tail-withdrawal assay, FIG. 13B, and in the CCI model, FIG. 13C. The CPP data indicated that OLKOR-L1 and its analogue OLKOR-L1-5HTrp do not produce reward in mice, characteristic of morphine. However, OLKOR-L1-5HTrp produced CPA in mice, much like the KOR agonist U50,488 used as a control. Conditioned place aversion was not observed for the parent peptide OLKOR-L1, suggesting a possibility that this undesired effect can be eliminated by further structural optimization.

Following intranasal administration of OLKOR-L1 or its analogue OLKOR-L1-5HTrp to knockout (KO) mice lacking MOR, DOR or KOR, the tail withdrawal test showed a significantly decreased response in KOR-KO mice, suggesting that OLKOR-L1/OLKOR-L1-5HTrp-mediated antinociception was predominantly KOR-mediated.

Overall, OLKOR-L1 and its analogue OLKOR-L1-5HTrp are promising analgesic with efficacy comparable to clinically used drugs such as morphine and gabapentin in a battery of pain assays but with longer duration and fewer side effects.

Analysis of the mouse brain 30 min after intranasal delivery of OLKOR-L1-5HTrp using RP-HPLC method with electrochemical detection showed significant increase in 5-HTrp accumulation in the midbrain, FIG. 14. Anatomical and physiological studies identified the midbrain periaqueductal gray (PAG) and its descending projections to the rostral ventromedial medulla (RVM) and spinal cord dorsal horn, as a primary anatomical pathway mediating opioid-based analgesia. Thus, presence of OLKOR-L1-5HTrp and 5-HTrp in the mid brain may explain this peptide's analgesic activity.

These data clearly demonstrated that using the approach of grafting (conjugating) a bioactive sequence (biologically active peptide or protein) into the OL scaffold (SEQ ID NO: 1) described herein can not only deliver known opioid peptide ligands into the brain, but also can generate novel ligands with improved activity and without undesirable side effects.

Figure 15A:
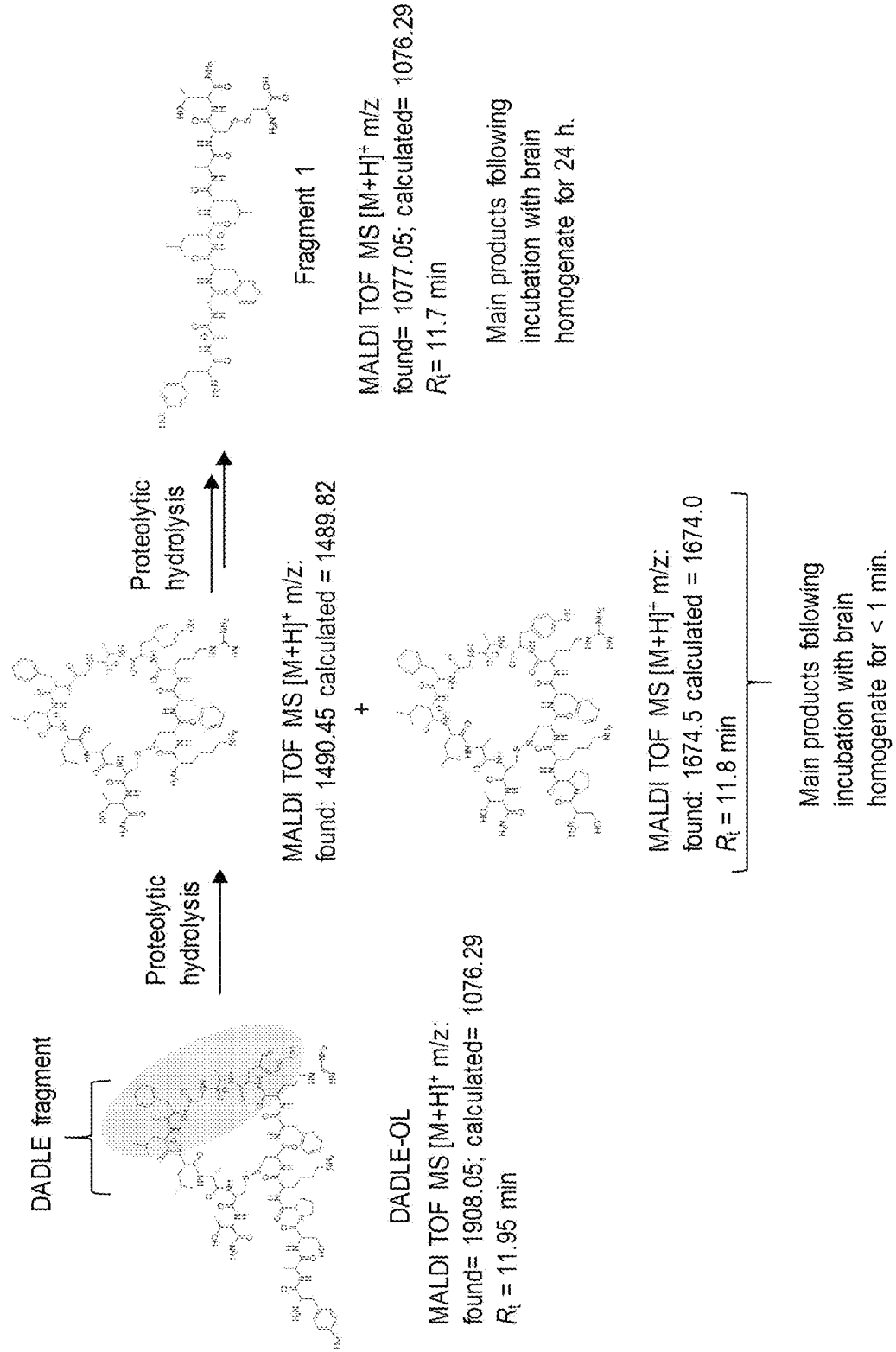
FIG. 15A shows amino acid structures and proteolytic hydrolysis of DADLE-OL.
Figure 15B:
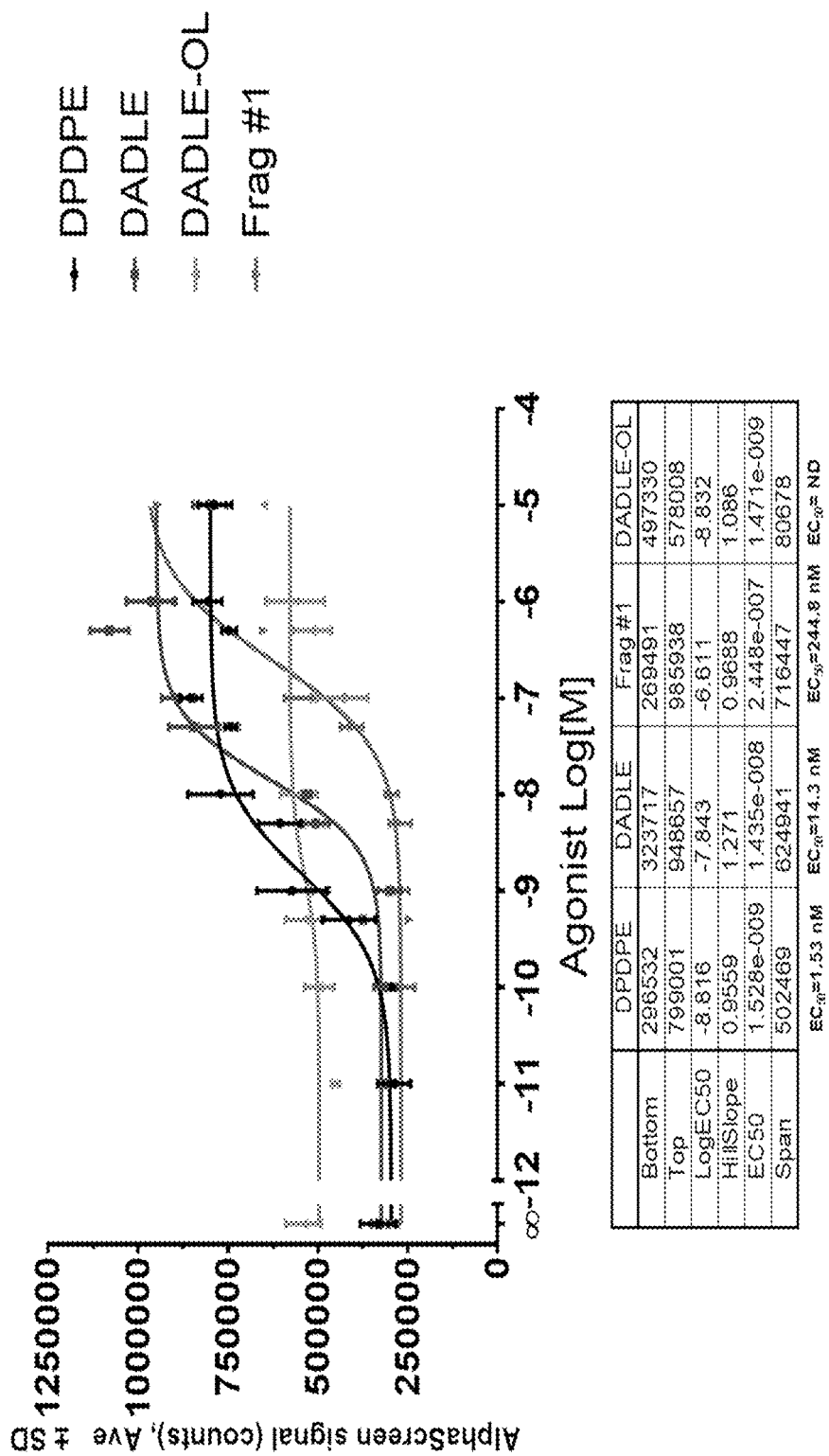
FIG. 15B is a graph showing the effects of DADLE-OL fragments on cAMP production. DPDPE=[D-Pen$^{2,5}$]-Enkephalin hydrate, a selective agonist for DOR, used as a control. DADLE=[D-Ala$^2$, D-Leu$^5$] enkephalin mixed MOR and DOR agonist, used as a control.

Peptides Stability Under Physiologically Relevant Conditions and Mode of Action Stability of DADLE-OL in 100% human cerebrospinal fluid and 100% mouse brain homogenate at 37° C. was determined. The disappearance of the intact peptides and formation of proteolytic products was monitored by RP-HPLC and MALDI TOF mass spectrometry. As in the case of the natural product OL, proteolytic cleavage of the N-terminal $Tyr^1$ and $Ala^2$ in the DADLE OL was observed almost immediately in the 100% mouse brain homogenate. After incubation for 24 hours the fragment 1 is isolated as the only remaining fragment (shown in FIG. 15). In contrast, no degradation of DADLE-OL was observed in 100% human CSF even after incubation for 24 h. These data suggest that DADLE-OL acts as a prodrug. Once diffused into the brain, DOR active sequence is released due to proteolytic hydrolysis of DADLE-OL. Fragment 1 was synthesized, and activities of the parent DADLE-OL and fragment 1 were tested in the cAMP inhibition assay (cAMP AlphaScreen™ Assay, Perkin Elmer). As shown in FIG. 15B, fragment 1 inhibited cAMP production with IC50 value of 26.8 nM, whereas no activity was observed for the cyclic peptide DADLE-OL under the same experimental conditions. These data suggest that DADLE-OL acts as a prodrug.

OTHER EMBODIMENTS

Any improvement may be made in part or all of the cyclic peptides, cyclic peptide conjugates, composition, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A conjugate comprising a cyclic peptide of SEQ ID NO: 6 conjugated to $(X)_m$ at the N-terminal end, wherein $(X)_m$ is an opioid receptor ligand or analogue thereof present in the central nervous system or a pharmaceutically acceptable salt thereof, and wherein the residues Xaa at positions 8-12 of SEQ ID NO: 6 consist of an opioid receptor ligand or analogue thereof present in the central nervous system or a pharmaceutically acceptable salt thereof, and wherein the conjugate has antinociceptive and analgesic activity.

2. The conjugate of claim 1, wherein the opioid receptor ligand is a δ opioid receptor (DOR) antagonist, a DOR agonist, a μ opioid receptor (MOR) antagonist, a MOR agonist, a κ opioid receptor (KOR) antagonist, or a KOR agonist.

3. The conjugate of claim 1, wherein the conjugate modulates opioid receptor activity.

4. A cyclic peptide comprising the amino acid sequence selected from the group consisting of $$\text{DADLE-OL} = Y^1A^2S^3P^4K^5\text{-}cyclo[C^6F^7R^8Y^9a^{10}G^{11}F^{12}I^{13}L^{14}A^{15}C^{16}]T^{17}; \quad (\text{SEQ ID NO: 8})$$

$$\text{DADLE-OL II} = Y^1a^2G^3F^4I^5K^6\text{-}cyclo[C^7F^8R^9Y^{10}P^{11}N^{12}G^{13}V^{14}L^{15}A^{16}C^{17}]T^{18}; \quad (\text{SEQ ID NO: 9})$$

$$\text{TIPP-OL} = Y^1A^2S^3P^4K^5\text{-}cyclo[C^6F^7R^8Y^9Tic^{10}F^{11}F^{12}V^{13}L^{14}A^{15}C^{16}]T^{17}; \quad (\text{SEQ ID NO: 10})$$

$$\text{TIPP-EM1-OL.} = Y^1P^2W^3F^4K^5\text{-}cyclo[C^6F^7R^8Y^9Tic^{10}F^{11}F^{12}V^{13}L^{14}A^{15}C^{16}]T^{17}; \quad (\text{SEQ ID NO: 7})$$

$$\text{OLKOR-L1} = Y^1A^2S^3P^4K^5\text{-}cyclo[C^6F^7R^8G^9F^{10}W^{11}P^{12}K^{13}L^{14}A^{15}C^{16}]T^{17}; \quad (\text{SEQ ID NO: 11})$$

and $$\text{OLMOR-L1} = Y^1A^2S^3P^4K^5\text{-}cyclo[C^6F^7R^8H^9F^{10}P^{11}V^{12}N^{13}L^{14}A^{15}C^{16}]T^{17}, \quad (\text{SEQ ID NO: 12})$$

wherein a=D-Ala and l=D-Leu.

5. The conjugate of claim 1, wherein a therapeutic agent is conjugated to $(X)_m$.

6. The conjugate of claim 5, wherein the therapeutic agent is a small molecule.

7. The conjugate of claim 5, wherein the therapeutic agent is selected from the group consisting of an analgesic, an anti-convulsant, an antidote, an anti-microbial, an anti-cancer, an anti-inflammatory, and an anti-neurodegenerative.

8. The conjugate of claim 6, wherein the small molecule is selected from the group consisting of 5-hydroxytryptophan (5HTrp), naloxone, serotonin, dopamine, L-3,4-dihydroxyphenylalanine (L-DOPA), epinephrine, norepinephrine, histamine, adenosine triphosphate, adenosine, cannabidiol (CBD), CBD derivative, tetrahydrocannabinol (THC), THC derivative, selective serotonin reuptake inhibitor, serotonin— norepinephrine reuptake inhibitor (SNRI), memantine, and pramipexole.

9. A cyclic peptide conjugate comprising the amino acid sequence:
5-HTrp$^1$-A$^2$S$^3$P$^4$K$^5$-cyclo[C$^6$F$^7$R$^8$G$^9$F$^{10}$W$^{11}$P$^{12}$K$^{13}$L$^{14}$A$^{15}$C$^{16}$]T$^{17}$ (SEQ ID NO: 13).

10. The conjugate of claim 5, wherein the therapeutic agent is a protein.

11. The conjugate of claim 10, wherein the protein is a growth hormone.

12. The conjugate of claim 5, wherein the therapeutic agent is an opioid receptor ligand or analogue thereof.

13. The conjugate of claim 12, wherein the opioid receptor ligand is a DOR antagonist, a DOR agonist, a MOR antagonist a MOR agonist, a KOR antagonist, or a KOR agonist.

14. A conjugate comprising a cyclic peptide of SEQ ID NO: 16 having conjugated to its N-terminus a therapeutic agent, wherein the therapeutic agent is conjugated to the N-terminus via a cleavable bond or linker.

15. The conjugate of claim 14, wherein the therapeutic agent is a small molecule selected from the group consisting of 5HTrp, naloxone, serotonin, dopamine, L-DOPA, epinephrine, norepinephrine, histamine, adenosine triphosphate, adenosine, cannabidiol (CBD), CBD derivative, tetrahydrocannabinol (THC), THC derivative, nabilone, selective serotonin reuptake inhibitor, fluvoxamine, serotonin-norepinephrine reuptake inhibitor (SNRI), desvenlafaxine, milnacipran, levomilnacipran, memantine, and pramipexole.

16. A cyclic peptide conjugate comprising the sequence SEQ ID NO: 17.

17. A composition for intranasal administration comprising a therapeutically effective amount of the conjugate of claim 1 and a pharmaceutically acceptable carrier.

18. A method of treating pain in an individual comprising administering to the individual in need thereof a composition comprising a cyclic peptide comprising the amino acid sequence of SEQ ID NO: 11 or SEQ ID NO: 13 via intranasal delivery to the individual's brain.

19. The method of claim 18, wherein the pain is neuropathic pain.

20. A conjugate comprising a cyclic peptide of SEQ ID NO: 6
conjugated to a small molecule,
wherein the residues Xaa at positions 8-12 of SEQ ID NO: 6 consist of an opioid receptor ligand or analogue thereof present in the central nervous system or a pharmaceutically acceptable salt thereof, and
wherein the conjugate has antinociceptive and analgesic activity, and
wherein the small molecule is selected from the group consisting of nabilone, fluvoxamine, desvenlafaxine, milnacipran, and levomilnacipran.

21. A conjugate comprising a cyclic peptide of SEQ ID NO: 16 having directly conjugated to its N-terminus a therapeutic agent.

22. The conjugate of claim 21, wherein the therapeutic agent is a small molecule selected from the group consisting of 5HTrp, naloxone, serotonin, dopamine, L-DOPA, epinephrine, norepinephrine, histamine, adenosine triphosphate, adenosine, cannabidiol (CBD), CBD derivative, tetrahydrocannabinol (THC), THC derivative, nabilone, selective serotonin reuptake inhibitor, fluvoxamine, serotonin-norepinephrine reuptake inhibitor (SNRI), desvenlafaxine, milnacipran, levomilnacipran, memantine, and pramipexole.

23. The conjugate of claim 21, wherein the therapeutic agent is a peptide.

* * * * *